(12) United States Patent
Koshino et al.

(10) Patent No.: US 10,987,081 B2
(45) Date of Patent: Apr. 27, 2021

(54) RADIATION IMAGING SYSTEM AND TRANSMISSION DEVICE

(71) Applicant: FUJIFILM Corporation, Tokyo (JP)

(72) Inventors: Riko Koshino, Tokyo (JP); Yusuke Maruo, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/846,432

(22) Filed: Apr. 13, 2020

(65) Prior Publication Data
US 2020/0397397 A1 Dec. 24, 2020

(30) Foreign Application Priority Data

Jun. 21, 2019 (JP) .................................. 2019-115668

(51) Int. Cl.
| | |
|---|---|
| *G08B 23/00* | (2006.01) |
| *A61B 6/00* | (2006.01) |
| *G06T 11/00* | (2006.01) |
| *G08B 21/04* | (2006.01) |
| *G16H 30/40* | (2018.01) |
| *A61B 6/02* | (2006.01) |
| *A61B 6/04* | (2006.01) |
| *A61B 90/00* | (2016.01) |

(52) U.S. Cl.
CPC ................. *A61B 6/56* (2013.01); *A61B 6/025* (2013.01); *A61B 6/461* (2013.01); *A61B 6/54* (2013.01); *G06T 11/005* (2013.01); *G08B 21/0453* (2013.01); *G16H 30/40* (2018.01); *A61B 6/0414* (2013.01); *A61B 6/502* (2013.01); *A61B 2090/065* (2016.02); *G06T 2207/30068* (2013.01)

(58) Field of Classification Search
CPC ........... A61B 6/56; A61B 6/025; A61B 6/461; A61B 6/54; G16H 30/40; G06T 11/005; G08B 21/0453

See application file for complete search history.

(56) References Cited

U.S. PATENT DOCUMENTS

| | | | |
|---|---|---|---|
| 5,323,007 A * | 6/1994 | Wernick ................ | G06T 11/005 250/363.03 |
| 7,760,924 B2 | 7/2010 | Ruth et al. | |
| 9,855,013 B2 | 1/2018 | Morita et al. | |
| 2016/0151035 A1* | 6/2016 | Noda ..................... | A61B 6/025 378/26 |
| 2016/0206273 A1* | 7/2016 | Fukuda .................... | A61B 6/54 |
| 2018/0114312 A1* | 4/2018 | Palma .................... | G06T 15/08 |

FOREIGN PATENT DOCUMENTS

| | | |
|---|---|---|
| JP | 2014128716 | 7/2014 |
| JP | 2014195622 | 10/2014 |

* cited by examiner

*Primary Examiner* — Phung Nguyen
(74) *Attorney, Agent, or Firm* — JCIPRNET

(57) ABSTRACT

There are provided a radiation imaging system and a transmission device capable of reducing a user's standby time compared to a case where a tomographic image is transmitted. A console acquires a plurality of projection images obtained by tomosynthesis imaging, generates a plurality of tomographic images by reconstruction using the plurality of projection images, synthesizes a 2-dimensional image based on the plurality of tomographic images, transmits the synthesized 2-dimensional image to an image interpretation support device, and transmits the plurality of projection images to the image interpretation support apparatus.

20 Claims, 16 Drawing Sheets

RADIATION IMAGING SYSTEM AND TRANSMISSION DEVICE

CROSS-REFERENCE TO RELATED APPLICATIONS

The present application claims priority under 35 U.S.C. § 119 to Japanese Patent Application No. 2019-115668 filed on Jun. 21, 2019, Each of the above application is hereby expressly incorporated by reference, in its entirety, into the present application.

BACKGROUND OF THE INVENTION

1. Field of the Invention

The present disclosure relates to a radiation imaging system and a transmission device.

2. Description of the Related Art

As an example of a radiation imaging system, a mammography apparatus in which a breast is used as a subject is known, and tomosynthesis imaging is performed in the mammography apparatus (for example, see JP2014-195622A). In the tomosynthesis imaging, a radiation source is moved to a plurality of positions with respect to a radiation detector, and radiation is emitted from the radiation source at each position. Then, a plurality of tomographic images corresponding to a plurality of tomographic planes of a breast are generated from a plurality of projection images obtained in this way.

At the time of image interpretation, a user such as an image interpreter interprets a tomographic image, and also interprets a 2-dimensional image. For example, the user produces a rough idea of a location of a lesion such as calcification in a 2-dimensional image, searches for a tomographic image of a tomographic plane where the lesion exists, and interprets the searched tomographic image in detail.

This 2-dimensional image is obtained by, for example, so-called simple imaging in which a radiation source is disposed on a normal line passing through the center of a detection surface of a radiation detector toward the detection surface to emit radiation. Further, a technique for generating a 2-dimensional image by combining a plurality of tomographic images has been proposed (for example, see JP2014-128716A).

SUMMARY OF THE INVENTION

However, in many cases, the number of tomographic images is larger than the number of projection images. In this case, in a case where the tomographic images are transmitted from the mammography apparatus to a terminal device used by the user for interpretation by the user, a communication load increases. As a result, a waiting time of the user becomes longer.

The present disclosure has been made in consideration of the above circumstances, and provides a radiation imaging system and a transmission device capable of reducing a user's standby time compared with a case where tomographic images are transmitted.

According to an aspect of the present disclosure, there is provided a radiation imaging system comprising a transmission device and a reception device, in which the transmission device includes: a projection image acquisition unit that acquires a plurality of projection images respectively corresponding to a plurality of positions and obtained by tomosynthesis imaging in which a subject is irradiated with radiation from a radiation source at the plurality of positions; at least one of a composite 2-dimensional image generating unit that generates a plurality of tomographic images by reconstruction using the plurality of projection images and generates a composite 2-dimensional image on the basis of the plurality of tomographic images, or a 2-dimensional image acquisition unit that acquires a 2-dimensional image obtained by irradiating the subject with radiation having a higher dose than that in the tomosynthesis imaging from the radiation source at one position; and a transmission unit that transmits at least one of the composite 2-dimensional image or the 2-dimensional image to the reception device, and transmits the plurality of projection images to the reception device; and in which the reception device includes: a reception unit that receives at least one of the composite 2-dimensional image or the 2-dimensional image transmitted by the transmission apparatus, and the plurality of projection images; a generating unit that generates a plurality of tomographic images by reconstruction using the plurality of projection images; and a display control unit that performs a control for displaying at least one of the composite 2-dimensional image or the 2-dimensional image, and the tomographic image on a display unit.

In the radiation imaging system according to the present disclosure, the transmission unit may transmit at least one of the composite 2-dimensional image or the 2-dimensional image to the reception device, and then, transmits the plurality of projection images to the reception device.

In the radiation imaging system according to the present disclosure, the transmission unit may transmit the plurality of projection images to the reception device, and then, transmits at least one of the composite 2-dimensional image or the 2-dimensional image to the reception device.

In the radiation imaging system according to the present disclosure, the display control unit may perform a control for displaying at least one of the composite 2-dimensional image or the 2-dimensional image, and the tomographic image on the display unit according to a preset display rule.

In the radiation imaging system according to the present disclosure, the display rule may include an execution order of a plurality of display steps, and the number and type of images to be displayed in each display step.

Further, in the radiation imaging system according to the present disclosure, the plurality of display steps may include a display step of displaying at least one of the composite 2-dimensional image or the 2-dimensional image at a preset display position, and a display step of displaying both of at least one of the composite 2-dimensional image or the 2-dimensional image and the tomographic image at the display position.

Further, in the radiation imaging system according to the present disclosure, the display control unit may perform, in each of the display steps, in a case where at least one of images to be displayed has not been received, a control for skipping display of the unreceived image and displaying only the received image.

Further, the radiation imaging system according to the present disclosure may be configured such that the reception device includes an acceptance unit that accepts an operation of ending display on the display unit from a user; a determination unit that determines whether all images to be displayed in the respective display steps have been displayed on the display unit; and a notification unit that notifies the user of a warning, in a case where the acceptance unit accepts the operation of ending the display before the determination unit determines that all the images to be displayed in the respective display steps have been displayed on the display unit.

Further, in the radiation imaging system of the present disclosure, the reception device may further include: a determination unit that determines whether all images to be displayed in the respective display steps have been displayed on the display unit; and a notification unit that notifies that the display is completed, in a case where the determination unit determines that all the images to be displayed in the respective display steps have been displayed on the display unit.

In the radiation imaging system according to the present disclosure, the display control unit may perform a control for further displaying a list of all image types displayed according to the display rule on the display unit.

In the radiation imaging system of the present disclosure, images that can be displayed according to the display rule and images that cannot be displayed according to the display rule may be identifiably displayed in the list.

Further, according to another aspect of the present disclosure, there is provided a transmission device comprising: a projection image acquisition unit that acquires a plurality of projection images respectively corresponding to a plurality of positions and obtained by tomosynthesis imaging in which a subject is irradiated with radiation from a radiation source at the plurality of positions; at least one of a composite 2-dimensional image generating unit that generates a plurality of tomographic images by reconstruction using the plurality of projection images and generates a composite 2-dimensional image on the basis of the plurality of tomographic images, or a 2-dimensional image acquisition unit that acquires a 2-dimensional image obtained by irradiating the subject with radiation having a higher dose than that in the tomosynthesis imaging from the radiation source at one position; and a transmission unit that transmits at least one of the composite 2-dimensional image or the 2-dimensional image to the reception device, and transmits the plurality of projection images to the reception device.

According to the present disclosure, it is possible to reduce a user's standby time compared with a case where tomographic images are transmitted.

DESCRIPTION OF THE PREFERRED EMBODIMENTS

Hereinafter, embodiments of the technique of the present disclosure will be described in detail with reference to the drawings.

Figure 1:
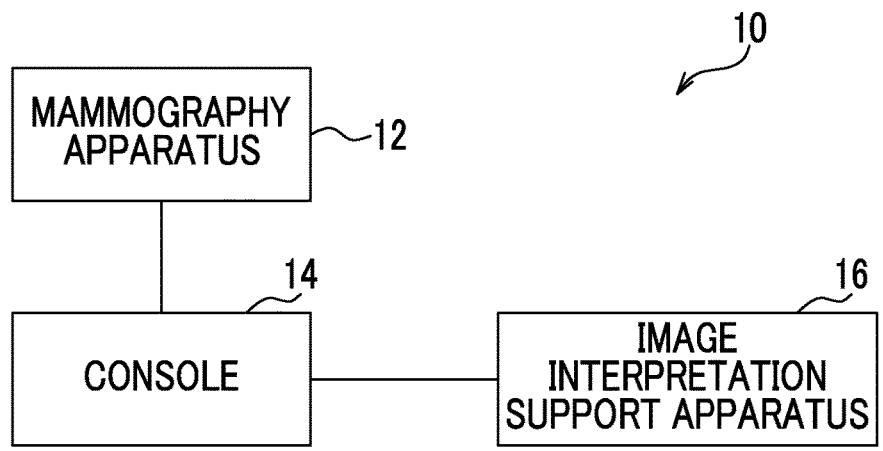
FIG. 1 is a block diagram showing an example of a configuration of a radiation imaging system.

First, a configuration of a radiation imaging system 10 according to an embodiment will be described with reference to FIG. 1. As shown in FIG. 1, the radiation imaging system 10 includes a mammography apparatus 12, a console 14, and an image interpretation support apparatus 16. The mammography apparatus 12 and the console 14 are communicably connected to each other, and the console 14 and the image interpretation support apparatus 16 are communicably connected to each other. The mammography apparatus 12 and the console 14 are operated by a photographer such as a technician, and the image interpretation support apparatus 16 is operated by an image interpreter such as a doctor.

Next, a configuration of the mammography apparatus 12 according to the present embodiment will be described with reference to FIGS. 2 to 4. The mammography apparatus 12 is an apparatus that irradiates the breast of an examinee as a subject, with radiation R (for example, X-rays) and captures a radiographic image of the breast. Further, the mammography apparatus 12 may be an apparatus that images the breast of the examinee in a state (sitting state) where the examinee is sitting in a chair (including a wheelchair), as well as a state (standing state) where the examinee is standing.

Figure 2:
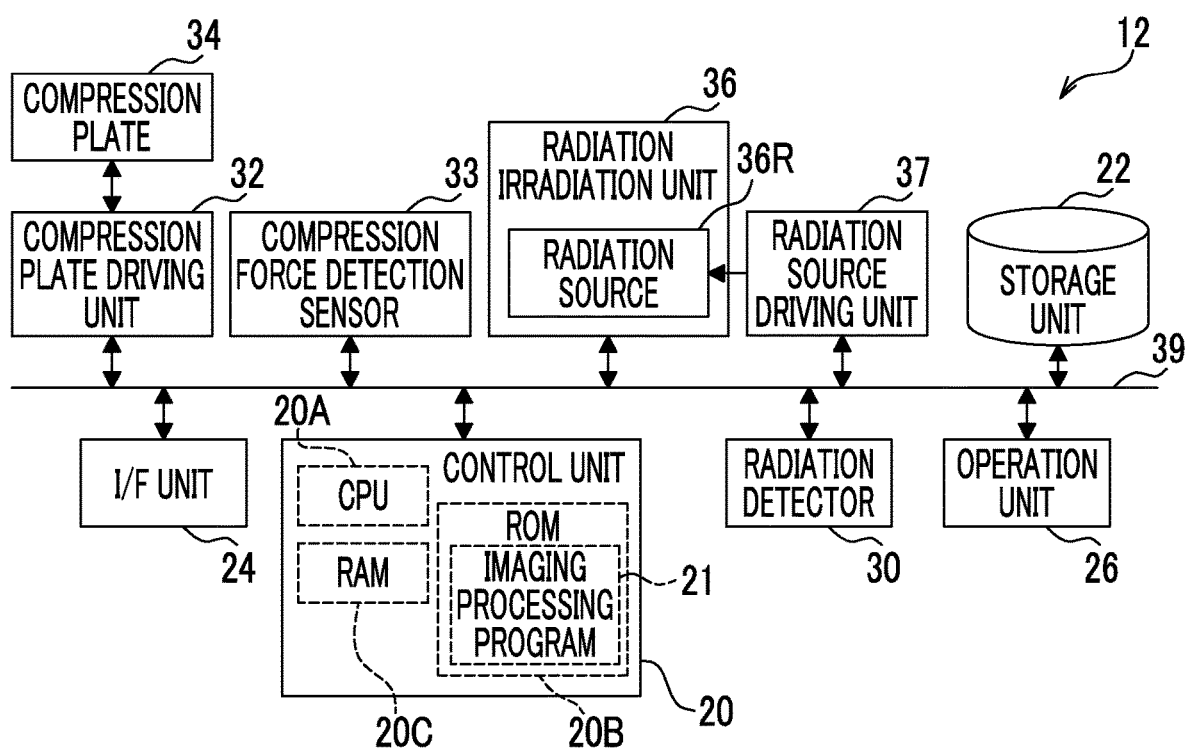
FIG. 2 is a block diagram showing an example of a hardware configuration of a mammography apparatus.

As shown in FIG. 2, the mammography apparatus 12 includes a control unit 20, a storage unit 22, an I/F (Interface) unit 24, an operation unit 26, a radiation detector 30, a compression plate driving unit 32, a compression force detection sensor 33, a compression plate 34, a radiation irradiation unit 36, and a radiation source driving unit 37. The control unit 20, the storage unit 22, the I/F unit 24, the operation unit 26, the radiation detector 30, the compression plate driving unit 32, the compression force detection sensor 33, the radiation irradiation unit 36, and the radiation source driving unit 37 are connected to each other through a bus 39 so that various kinds of information can be exchanged therebetween.

The control unit 20 controls an overall operation of the mammography apparatus 12 under the control of the console 14. The control unit 20 includes a CPU (Central Processing Unit) 20A, a ROM (Read Only Memory) 20B, and a RAM (Random Access Memory) 20C. The ROM 20B stores in advance various programs and the like, including an imaging processing program 21 for performing control relating to imaging for a radiographic image, which is executed by the CPU 20A. The RAM 20C temporarily stores various data.

The radiation detector 30 detects the radiation R that has passed through the breast that is a subject. As shown in FIG. 3, the radiation detector 30 is disposed inside an imaging table 40. In the mammography apparatus 12 according to the present embodiment, in a case where imaging is performed, the breast of an examinee is positioned on an imaging plane 40A of the imaging table 40 by the photographer. The imaging plane 40A with which the breast of the examinee is in contact is made of, for example, carbon or the like from the viewpoint of transmittance of the radiation R and the strength.

The radiation detector 30 detects the radiation R passed through the breast of the examinee and the imaging table 40, generates a radiographic image on the basis of the detected radiation R, and outputs image data that represents the generated radiographic image. The type of the radiation detector 30 is not particularly limited. For example, the radiation detector 30 may be an indirect conversion type radiation detector that converts the radiation R into light and converts the converted light into electric charges, or may be a direct conversion type radiation detector that directly converts the radiation R into electric charges.

The storage unit 22 stores image data that represents a radiographic image captured by the radiation detector 30, a variety of other information, and the like. Specific examples of the storage unit 22 include a hard disk drive (HDD), a solid state drive (SSD), or the like. The I/F unit 24 communicates various kinds of information with the console 14 through wireless communication or wired communication. Image data that represents a radiographic image captured by the radiation detector 30 in the mammography apparatus 12 is transmitted to the console 14 through the I/F unit 24.

The operation unit 26 is provided as a plurality of switches, for example, on the imaging table 40 or the like of the mammography apparatus 12. The operation unit 26 may be provided as a touch panel type switch, or may be provided as a foot switch operated by a user with the user's feet.

The radiation irradiation unit 36 includes a radiation source 36R. As shown in FIG. 3, the radiation irradiation unit 36 is provided on an arm unit 42 together with the imaging table 40 and the compression unit 46. The mammography apparatus 12 according to the present embodiment includes the arm unit 42, a base 44, and a shaft 45. The arm unit 42 is held by the base 44 so as to be movable in an up-down direction (Z-axis direction). The shaft 45 connects the arm unit 42 to the base 44. Further, the arm unit 42 is relatively rotatable with respect to the base 44 using the shaft 45 as a rotation axis by the radiation source driving unit 37.

Figure 3:
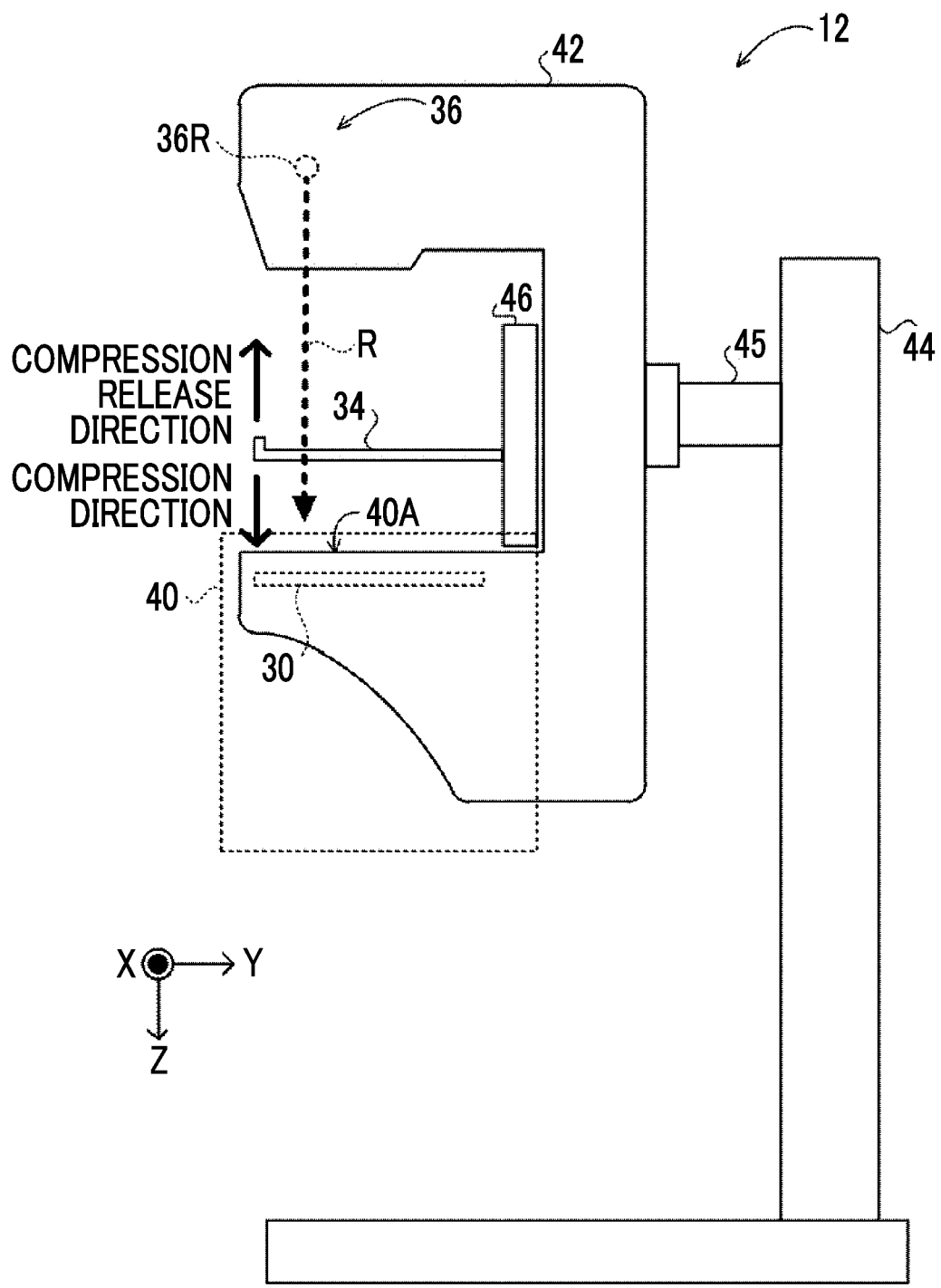
FIG. 3 is a side view showing an example of an external appearance of the mammography apparatus.
Figure 4:
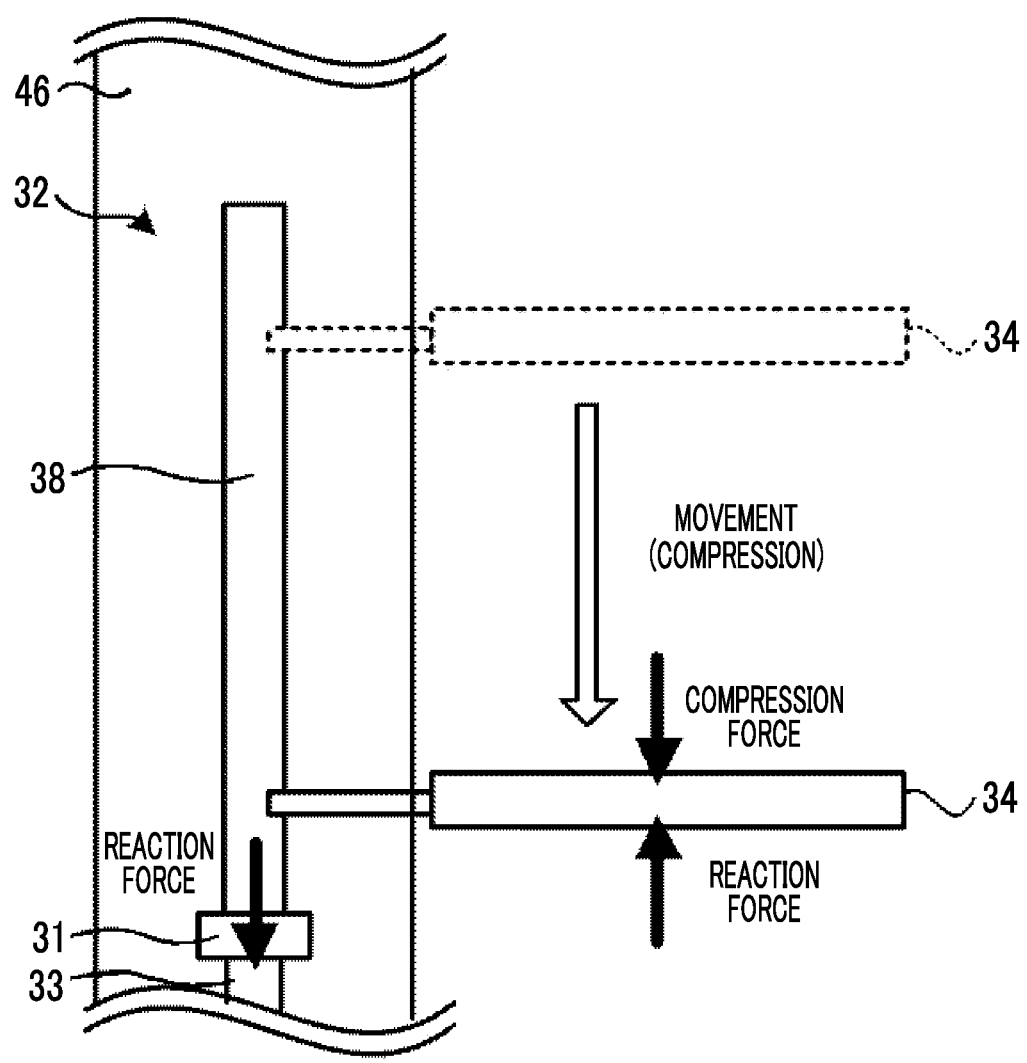
FIG. 4 is a diagram illustrating an example of a configuration in a case where a compression force is detected due to a load applied to a motor.

As shown in FIGS. 3 and 4, the compression plate driving unit 32, the compression force detection sensor 33, and the compression plate 34 are provided in the compression unit 46. The compression unit 46 and the arm unit 42 are relatively rotatable with respect to the base 44 in an independent manner using the shaft 45 as a rotation axis. In the present embodiment, a gear (not shown) is provided in each of the shaft 45, the arm unit 42, and the compression unit 46, and by performing switching between an engagement state and a disengagement state of the gears, the arm unit 42 and the compression unit 46 are connected to the shaft 45. One or both of the arm unit 42 and the compression unit 46 connected to the shaft 45 rotate integrally with the shaft 45.

The compression plate 34 according to the present embodiment is a plate-shaped compression member, and is moved in a vertical direction (Z-axis direction) by the compression plate driving unit 32 to compress the breast of the examinee between the compression plate 34 and the imaging table 40. Hereinafter, a direction in which the breast is compressed with respect to the direction of movement of the compression plate 34, in other words, a direction toward the imaging plane 40A is referred to as a "compression direction", and a direction in which the compression on the breast is released, in other words, a direction toward the radiation irradiation unit 36 is referred to as a "compression release direction". Further, it is preferable that the compression plate 34 is transparent in order to perform positioning in the compression of the breast and check of the compression state. In addition, the compression plate 34 is formed of a material having excellent transmission characteristics of the radiation R.

As shown in FIG. 4, in the compression unit 46, a compression plate driving unit 32 including a motor 31 and a ball screw 38, and a compression force detection sensor 33 are provided. The compression force detection sensor 33 detects a compression force for compressing the entire breast by the compression plate 34. The example of FIG. 4 shows a configuration in which the compression force detection sensor 33 detects a compression force on the basis of a load applied to the motor 31 that is a driving source of the compression plate 34. The compression plate 34 is supported by the ball screw 38, and slides between the imaging table 40 and the radiation source 36R as the motor 31 is driven. The compression force detection sensor 33 according to the present embodiment is a strain gauge such as a load cell, and the compression force detection sensor 33 detects a compression force for compressing the breast by the compression plate 34 by detecting a reaction force of the compression force by the compression plate 34.

A method for detecting the compression force is not limited to the configuration shown in FIG. 4, and for example, the compression force detection sensor 33 may be a semiconductor pressure sensor, a static capacitance pressure sensor, or the like. Further, for example, the compression plate 34 may be provided with the compression force detection sensor 33.

Figure 5:
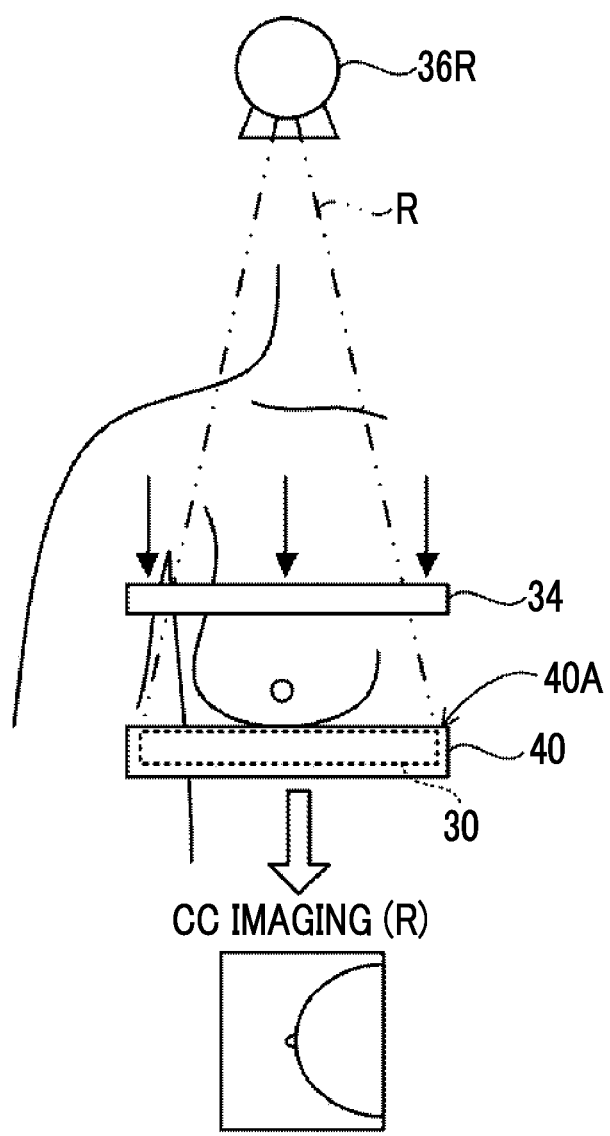
FIG. 5 is a diagram showing a state of CC imaging.
Figure 6:
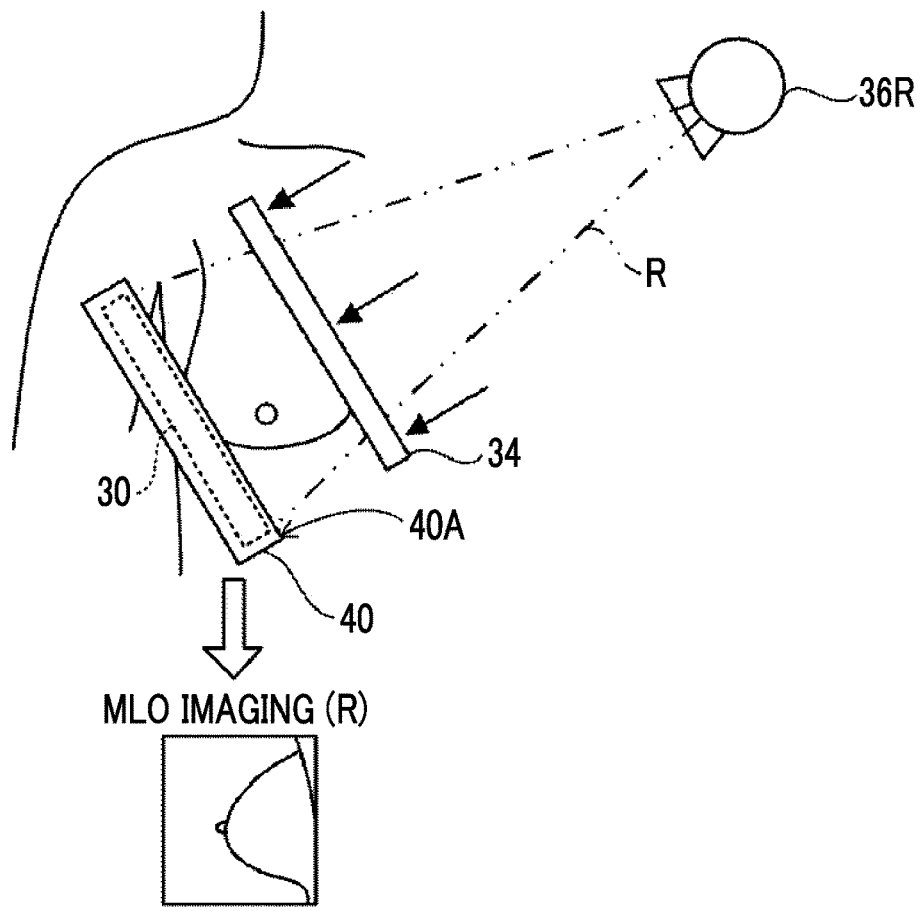
FIG. 6 is a diagram showing a state of MLO imaging.

FIG. 5 shows a state of simple imaging in which the radiation source 36R is disposed on a normal line passing through the center of the detection surface of the radiation detector 30 toward the detection surface to emit the radiation R, which is Cranio-Caudal (CC) imaging in which the breast is vertically interposed and compressed to perform imaging. On the other hand, FIG. 6 shows a state of simple imaging, which is medio-lateral oblique (MLO) imaging in which the breast is obliquely interposed and compressed to perform imaging. Hereinafter, a radiographic image generated by the radiation detector 30 by CC imaging is referred to as a "CC image", and a radiographic image generated by the radiation detector 30 by MLO imaging is referred to as an "MLO image". FIGS. 5 and 6 show examples in which the right breast is a subject, but CC imaging and MLO imaging are similarly performed for the left breast.

Further, in the mammography apparatus 12 according to the present embodiment, tomosynthesis imaging for irradiating the breast of a subject with the radiation R from the radiation source 36R at a plurality of positions is also performed. In the tomosynthesis imaging, the radiation source 36R of the radiation irradiation unit 36 is continuously moved by the radiation source driving unit 37 to each of a plurality of positions (hereinafter, referred to as "irradiation positions") having different irradiation angles (that is, projection angles) as the arm unit 42 is rotated.

Figure 7:
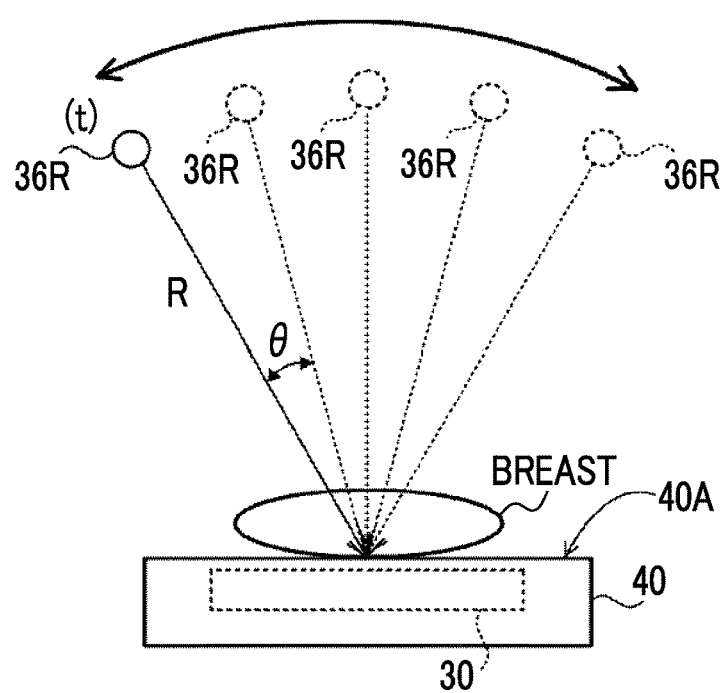
FIG. 7 is a diagram showing a state of tomosynthesis imaging.

As shown in FIG. 7, the radiation source 36R is moved to irradiation positions t (t=0, 1, . . . T, T=4 in the example of FIG. 7) having different irradiation angles by a predetermined angle θ, for example, in other words, to positions having different incident angles of the radiation R with respect to the detection surface of the radiation detector 30. At each irradiation position t, the radiation R is emitted from the radiation source 36R according to an instruction from the console 14, and a radiographic image is captured by the radiation detector 30. In the radiation imaging system 10, in a case where the tomosynthesis imaging is performed in which the radiation source 36R is moved to each irradiation position t and imaging for a radiographic image is performed at each irradiation position t, T projection images corresponding to the number of irradiation positions are obtained. In the tomosynthesis imaging, the CC imaging and the MLO imaging are also performed.

In the present embodiment, a configuration in which the radiation source 36R is moved to each irradiation position t by moving the radiation irradiation unit 36 has been described, but the invention is not limited thereto. For example, a configuration in which the mammography apparatus 12 includes a plurality of radiation sources 36R corresponding to the respective irradiation positions t may be used. Further, it is not essential that the angle θ is a constant value.

Figure 8:
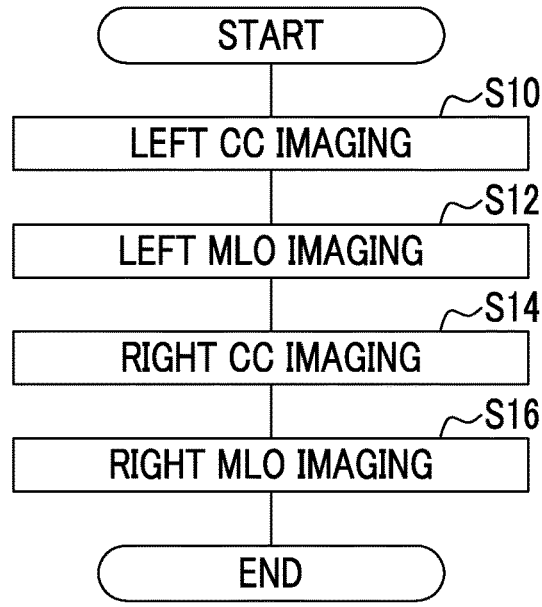
FIG. 8 is a flowchart showing an example of a tomosynthesis imaging process.

FIG. 8 shows a flowchart of a tomosynthesis imaging process by the mammography apparatus 12 according to the present embodiment. In step S10 in FIG. 8, the mammography apparatus 12 performs tomosynthesis imaging for the left breast using the CC imaging method, and transmits a plurality of projection images obtained by the imaging to the console 14. In step S12, the mammography apparatus 12 performs tomosynthesis imaging for the left breast using the MLO imaging method, and transmits a plurality of projection images obtained by the imaging to the console 14. In step S14, the mammography apparatus 12 performs tomosynthesis imaging for the right breast by the CC imaging method, and transmits a plurality of projection images obtained by the imaging to the console 14. In step S16, the mammography apparatus 12 performs tomosynthesis imaging for the right breast using the MLO imaging method, and transmits a plurality of projection images obtained by the imaging to the console 14. In a case where the process in step S16 ends, the tomosynthesis imaging process ends. The execution order of steps S10 to S16 is not limited to the example shown in FIG. 8. The console 14 receives the plurality of projection images transmitted from the mammography apparatus 12 in each of steps S10 to S16.

Hereinafter, the CC imaging for the left breast is referred to as "left CC imaging", and the MLO imaging for the left breast is referred to as "left MLO imaging". Hereinafter, CC imaging for the right breast is referred to as "right CC imaging", and MLO imaging for the right breast is referred to as "right MLO imaging".

Accordingly, in the tomosynthesis imaging process according to the present embodiment, the following four sets of a plurality of projection images are sequentially transmitted to the console 14. The plurality of projection images are not limited to four sets, and may be, for example, three sets among the four sets.

(1) The plurality of projection images obtained by performing tomosynthesis imaging in the left CC imaging.

(2) The plurality of projection images obtained by performing tomosynthesis imaging in the left MLO imaging.

(3) The plurality of projection images obtained by performing tomosynthesis imaging in the right CC imaging.

(4) The plurality of projection images obtained by performing tomosynthesis imaging in the right MLO imaging.

Figure 9:
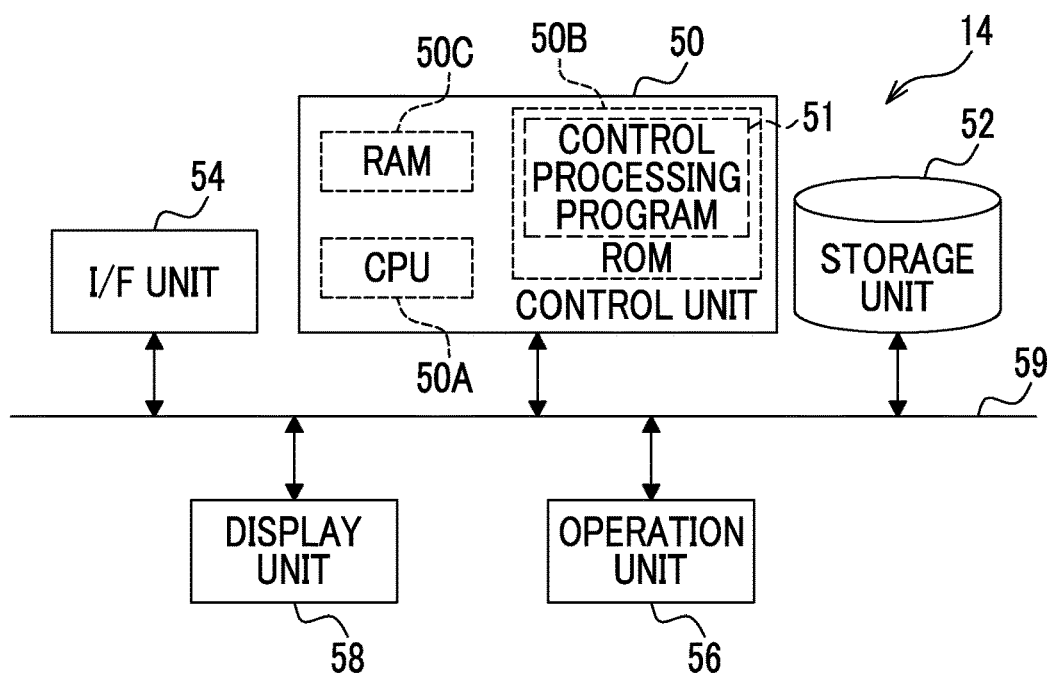
FIG. 9 is a block diagram showing an example of a hardware configuration of a console.

Next, a hardware configuration of the console 14 according to the present embodiment will be described with reference to FIG. 9. The console 14 inputs an imaging order and various information obtained from a radiology information system (RIS) or the like, and instructions given by a user through the operation unit 56 or the like, for example, to the mammography apparatus 12 through a network. As shown in FIG. 9, the console 14 includes a control unit 50, a storage unit 52, an I/F unit 54, an operation unit 56, and a display unit 58. The control unit 50, the storage unit 52, the I/F unit 54, the operation unit 56, and the display unit 58 are connected to each other through a bus 59 so that various kinds of information can be exchanged. Examples of the console 14 include information processing devices such as a personal computer and a server computer.

The control unit 50 controls an entire operation of the console 14. The control unit 50 includes a CPU 50A, a ROM 50B, and a RAM 50C. Various programs including a control processing program 51 executed by the CPU 50A are stored in the ROM 50B in advance. The RAM 50C temporarily stores various data. The storage unit 52 stores image data that represents a radiographic image captured by the mammography apparatus 12, various other information, and the like. Specific examples of the storage unit 52 include an HDD, an SSD, or the like.

The operation unit 56 is used by a user to input an instruction relating to imaging for a radiographic image including an irradiation instruction of the radiation R, various information, and the like. Accordingly, the operation unit 56 according to the present embodiment includes an irradiation instruction button to be pressed by the user in instructing irradiation of the radiation R. The operation unit 56 is not particularly limited, and includes, for example, various switches, a touch panel, a touch pen, a mouse, and the like. The display unit 58 displays various information. The operation unit 56 and the display unit 58 may be integrated into a touch panel display. The I/F unit 54 communicates various types of information with the mammography apparatus 12 and the image interpretation support apparatus 16 through wireless communication or wired communication.

Figure 10:
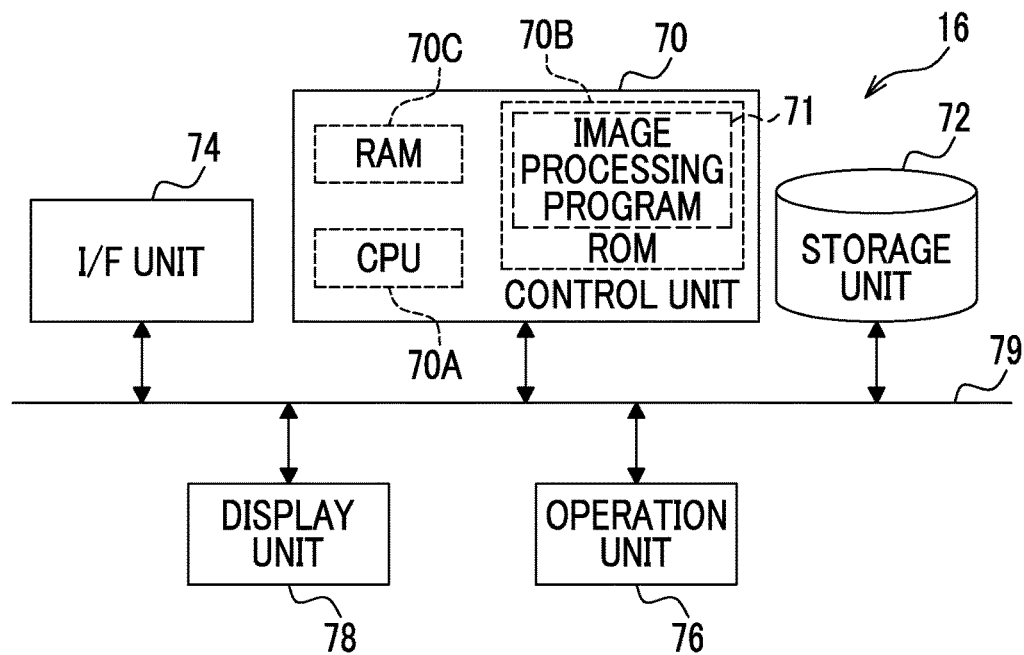
FIG. 10 is a block diagram showing an example of a hardware configuration of an image interpretation support apparatus.

Next, a hardware configuration of the image interpretation support apparatus 16 according to the present embodiment will be described with reference to FIG. 10. As shown in FIG. 10, the image interpretation support apparatus 16 includes a control unit 70, a storage unit 72, an I/F unit 74, an operation unit 76, and a display unit 78. The control unit 70, the storage unit 72, the I/F unit 74, the operation unit 76, and the display unit 78 are connected to each other through a bus 79 so that various kinds of information can be exchanged. Examples of the image interpretation support apparatus 16 include information processing devices such as a personal computer and a server computer.

The control unit 70 controls an overall operation of the image interpretation support apparatus 16. The control unit 70 includes a CPU 70A, a ROM 70B, and a RAM 70C. Various programs including an image processing program 71 executed by the CPU 70A are stored in the ROM 70B in advance. The RAM 70C temporarily stores various data. The storage unit 72 stores image data that represents a radiation image transmitted from the console 14, other various information, and the like. Specific examples of the storage unit 72 include an HDD, an SSD, or the like.

The operation unit 76 includes, for example, a mouse, a keyboard, and the like, and is used for an operation from a user. The display unit 78 displays various information. The operation unit 76 and the display unit 78 may be integrated into a touch panel display. The I/F unit 74 communicates various types of information with the console 14 through wireless communication or wired communication.

Figure 11:
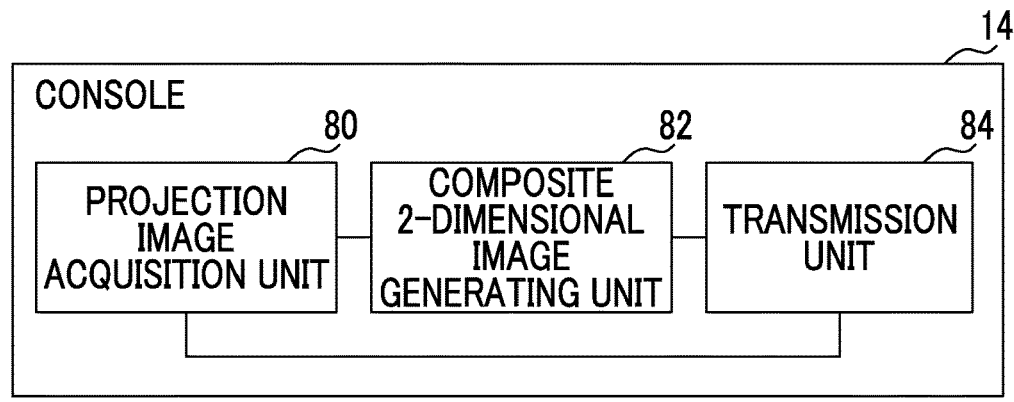
FIG. 11 is a block diagram showing an example of a functional configuration of the console.

Next, a functional configuration of the console 14 according to the present embodiment will be described with reference to FIG. 11. As shown in FIG. 11, the console 14 includes a projection image acquisition unit 80, a composite 2-dimensional image generating unit 82, and a transmission unit 84. As the CPU 50A executes the control processing program 51, the console 14 functions as the projection image acquisition unit 80, the composite 2-dimensional image generating unit 82, and the transmission unit 84. The console 14 is an example of a transmission device according to the disclosed technique. The projection image acquisition unit 80, the composite 2-dimensional image generating unit 82, and the transmission unit 84 have the following functions for each set among the four sets of the plurality of projection images.

Figure 12:
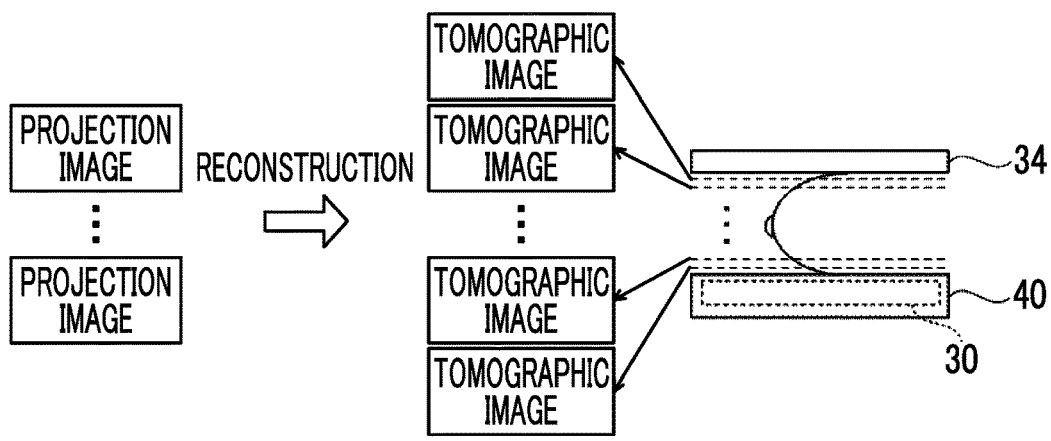
FIG. 12 is a diagram showing a state in which a plurality of tomographic images are generated from a plurality of projection images obtained by tomosynthesis imaging.

The projection image acquisition unit 80 acquires a plurality of (T in this embodiment) projection images corresponding to the plurality of irradiation positions t obtained by the tomosynthesis imaging through the control unit 20 of the mammography apparatus 12. As shown in FIG. 12, the composite 2-dimensional image generating unit 82 generates a plurality of tomographic images at a predetermined slice interval by performing reconstruction using the plurality of projection images acquired by the projection image acquisition unit 80. As a reconstruction method, for example, a known method such as a filtered back projection method may be used. This tomographic image is an image in which structures that exist on each of a plurality of tomographic planes of the breast are emphasized. In FIG. 12, the tomographic planes are indicated by broken straight lines. This tomographic planes are planes parallel to the detection plane of the radiation detector 30. Here, "parallel" means parallel within a range that allows an error caused by a temporal change of the mammography apparatus 12 and a change in environmental conditions. The slice interval means an interval between adjacent tomographic planes, and is 1 mm, for example.

Further, the composite 2-dimensional image generating unit 82 generates a composite 2-dimensional image on the basis of the plurality of generated tomographic images. For the generation of the composite 2-dimensional image, for example, a method disclosed in JP2014-128716A may be used. The method disclosed in JP2014-128716A is a method for generating a composite 2-dimensional image by projecting two or more tomographic images among a plurality of tomographic images, or at least one of the plurality of tomographic images and at least one projection image in a depth direction in which tomographic planes in a subject are arranged. The method for generating the composite 2-dimensional image is not limited to thereto. For example, a method for generating a combined 2-dimensional image by projecting two or more tomographic images among a plurality of tomographic images, or at least one of the plurality of tomographic images and at least one of a projection images in the depth direction in which the tomographic planes in the subject are arranged, using a minimum value projection method, may be used.

The transmission unit 84 transmits a composite 2-dimensional image generated by the composite 2-dimensional image generating unit 82 to the image interpretation support apparatus 16, and transmits a plurality of projection images acquired by the projection image acquisition unit 80 to the image interpretation support apparatus 16. In the present embodiment, the transmission unit 84 transmits the composite 2-dimensional image generated by thecomposite 2-dimensional image generating unit 82 to the image interpretation support apparatus 16, and then, transmits the plurality of projection images acquired by the projection image acquisition unit 80 to the image interpretation support apparatus 16. The transmission unit 84 may transmit the plurality of projection images acquired by the projection image acquisition unit 80 to the image interpretation support apparatus 16, and then, may transmit the composite 2-dimensional image generated by the composite 2-dimensional image generating unit 82 to the image interpretation support apparatus 16.

Figure 13:
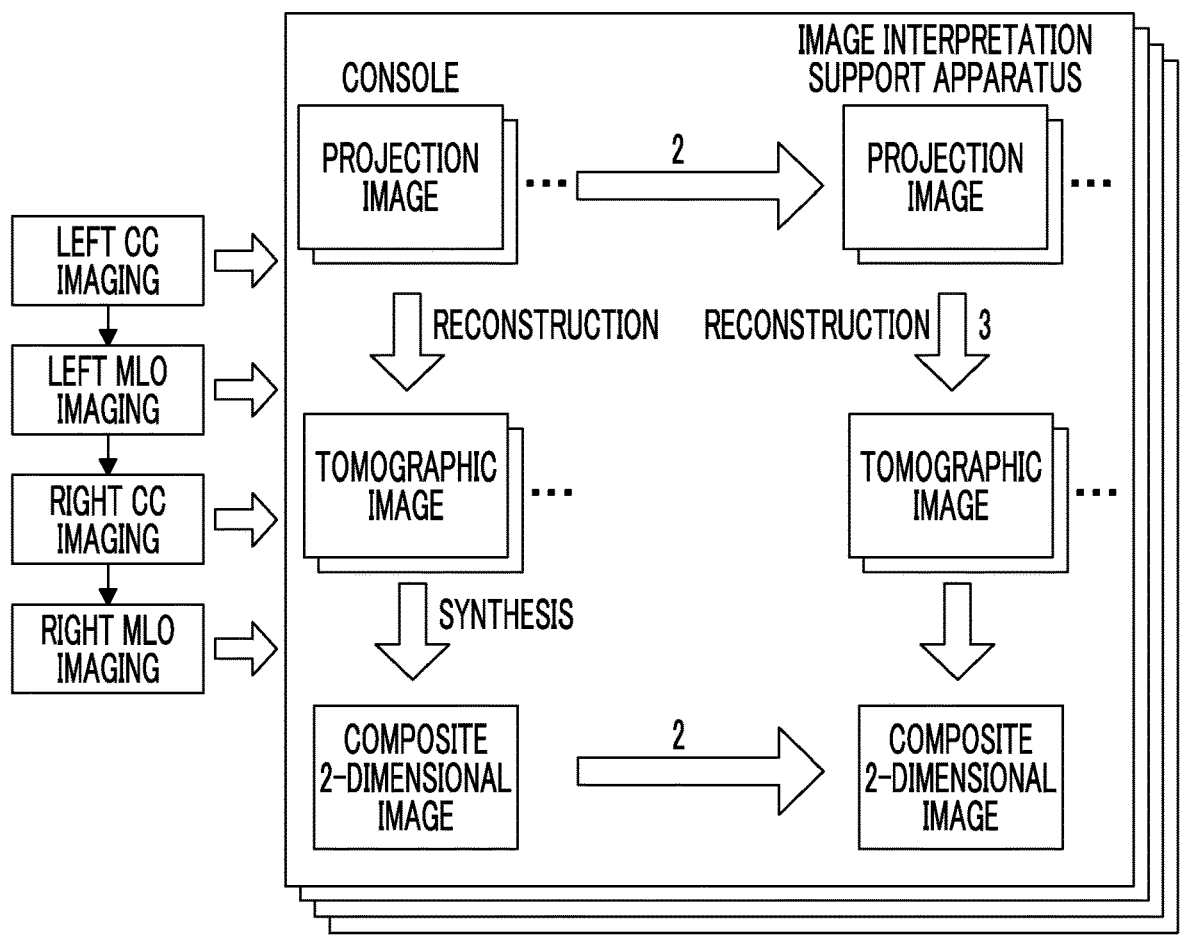
FIG. 13 is a diagram showing a transmission order of a projection image and a composite 2-dimensional image.

With the above configuration, as shown in FIG. 13, the console 14 transmits the composite 2-dimensional image and the plurality of projection images in the order of the composite 2-dimensional image and the plurality of projection images corresponding to each of steps S10 to S16 of the tomosynthesis imaging process, to the image interpretation support apparatus 16. The numbers "1", "2", and "3" in FIG. 13 indicate the order of execution.

Figure 14:
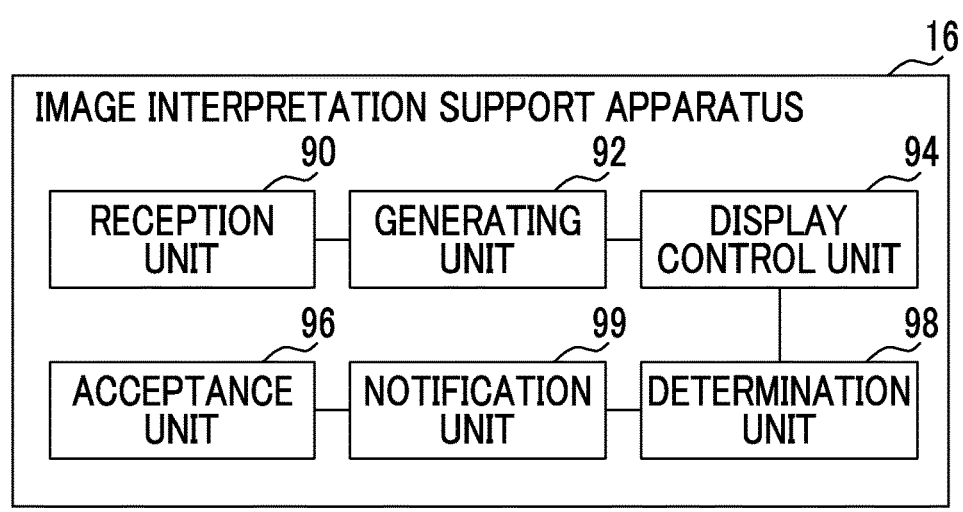
FIG. 14 is a block diagram showing an example of a functional configuration of the image interpretation support apparatus.

Next, a functional configuration of the image interpretation support apparatus 16 according to the present embodiment will be described with reference to FIG. 14. As shown in FIG. 14, the image interpretation support apparatus 16 includes a reception unit 90, a generating unit 92, a display control unit 94, an acceptance unit 96, a determination unit 98, and a notification unit 99. As the CPU 70A executes the image processing program 71, the image interpretation support apparatus 16 functions as the reception unit 90, the generating unit 92, the display control unit 94, the acceptance unit 96, the determination unit 98, and the notification unit 99. The image interpretation support apparatus 16 is an example of a reception device according to the disclosed technology.

The reception unit 90 receives a composite 2-dimensional image and a plurality of projection images transmitted by the console 14. The generating unit 92 generates a plurality of tomographic images on the basis of the plurality of projection images received by the reception unit 90, using the same method as in the composite 2-dimensional image generating unit 82 of the console 14. That is, as shown in FIG. 13, in each step of the tomosynthesis imaging process, the image interpretation support apparatus 16 may refer to the composite 2-dimensional image and the plurality of tomographic images in the order of the composite 2-dimensional image and the plurality of tomographic images.

The display control unit 94 performs a control for displaying the composite 2-dimensional image received by the reception unit 90 and the tomographic image generated by the generating unit 92 on the display unit 78. Specifically, the display control unit 94 performs a control for displaying the composite 2-dimensional image received by the reception unit 90 and the tomographic image generated by the generating unit 92 on the display unit 78 according to a preset display rule. This display rule may be referred to as a reading protocol. The display rule is defined in advance by an image interpreter. A specific example of the display rule according to the present embodiment will be described with reference to FIG. 15.

Figure 15:
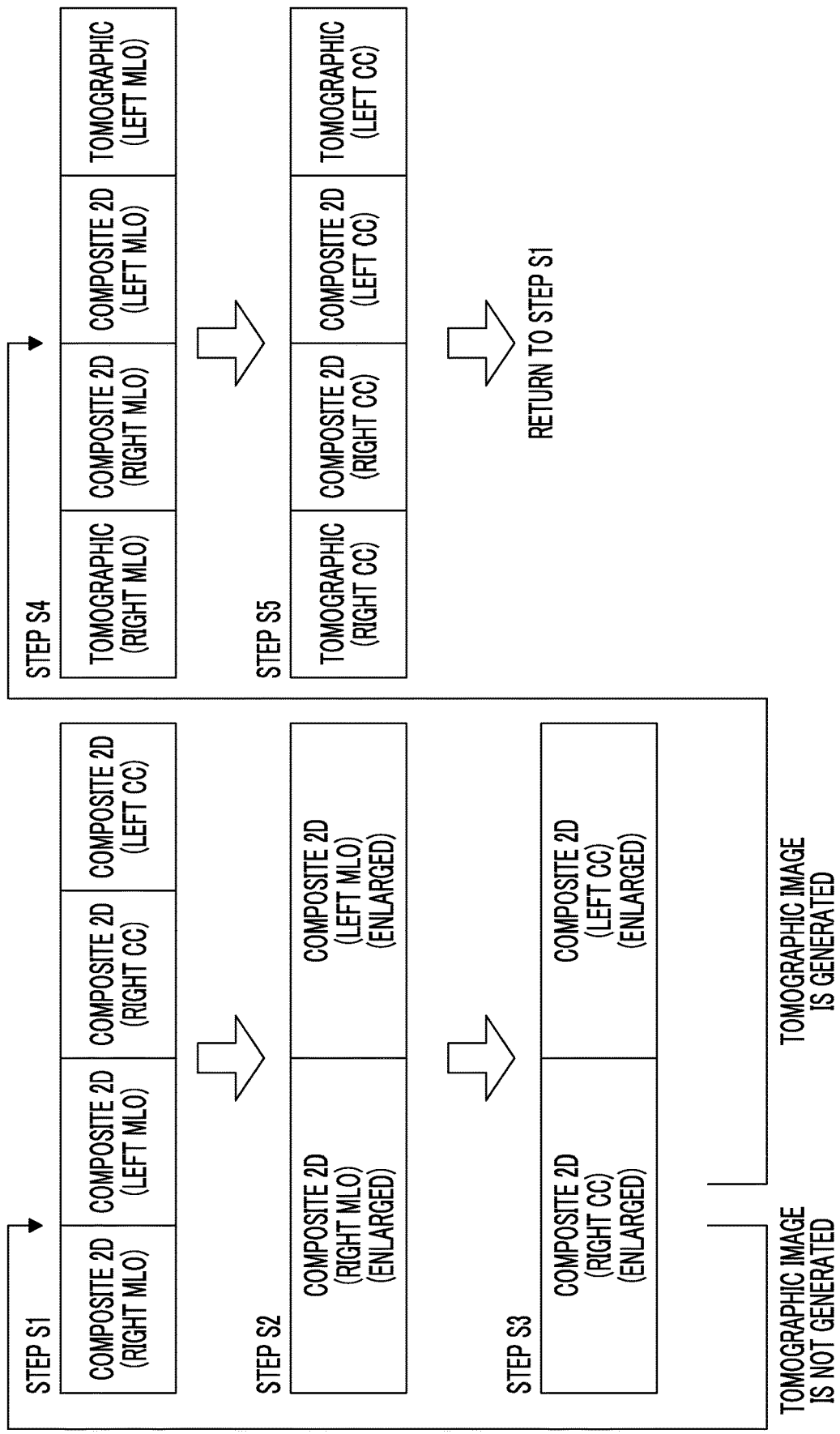
FIG. 15 is a diagram illustrating a display rule.

As shown in FIG. 15, the display rule according to the present embodiment includes an execution order of five display steps of display steps 1 to 5, and the number and type of images to be displayed in each display step. The number of display steps is not limited to five, and may be two or more and four or less, or six or more. Examples of the types of images to be displayed include images having different generation methods, such as a tomographic image and a composite 2-dimensional image, and images having different subjects and imaging directions, such as left MLO imaging, left CC imaging, right MLO imaging, and right CC imaging. Examples of the types of images to be displayed include images having different display magnifications of subjects. An image having a different display magnification of a subject is, for example, an image obtained by enlarging and displaying an image after imaging.

Each display step includes a display step of displaying a composite 2-dimensional image at a preset display position, and a display step of displaying both the composite 2-dimensional image and the tomographic image at the display position. In the example of FIG. 15, the display steps 1 to 3 are display steps for displaying the composite 2-dimensional image, and the display steps 4 and 5 are display steps for displaying both the composite 2-dimensional image and the tomographic image.

Specifically, the display step S1 is a display step of sequentially displaying, from the left, a composite 2-dimensional image generated as a result of the right MLO imaging (hereinafter, referred to as a "composite 2-dimensional image of right MLO") and a composite 2-dimensional image generated as a result of the left MLO imaging (hereinafter, referred to as a "composite 2-dimensional image of left MLO"), a composite 2-dimensional image generated as a result of the right CC imaging (hereinafter, referred to as a "composite 2-dimensional image of right CC"), and a composite 2-dimensional image generated as a result of the left CC imaging (hereinafter, referred to as a "composite 2-dimensional image of left CC").

The display step S2 is a display step of sequentially displaying, from the left, enlarged images obtained by enlarging respective breast portions of the composite 2-dimensional image of the right MLO and the composite 2-dimensional image of the left MLO. The display step S3 is a display step of sequentially displaying, from the left, enlarged images obtained by enlarging respective breast portions of the composite 2-dimensional image of the right CC and the composite 2-dimensional image of the left CC. In the present embodiment, the display steps 1 to 3 are repeated until at least one set of tomographic image groups is generated by the generating unit 92. These enlarged images are, for example, images obtained by enlarging the respective breast portions of the composite 2-dimensional image.

In a case where at least one set of tomographic image groups is generated by the generating unit 92, the display steps 4 and 5 may also be executed, and the display steps 1 to 5 are repeated. The display step S4 is a display step of sequentially displaying, from the left, a tomographic image group generated as a result of the right MLO imaging (hereinafter, referred to as a "tomographic image group of right MLO"), a composite 2-dimensional image of the right MLO, a composite 2-dimensional image of the left MLO, and a tomographic image group generated as a result of left MLO imaging (hereinafter, referred to as a "tomographic image group of the left MLO"). The display step S5 is a display step of sequentially displaying, from the left, a tomographic image group generated as a result of the right CC imaging (hereinafter, referred to as a "tomographic image group of right CC"), a composite 2-dimensional image of right CC, a composite 2-dimensional image of left CC, and a tomographic image group generated as a result of left CC imaging (hereinafter, referred to as a "tomographic image group of left CC").

Figure 16:
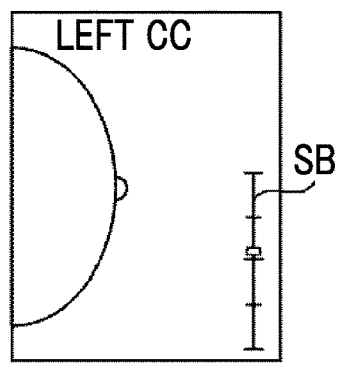
FIG. 16 is a diagram showing an example of a display mode of a tomographic image.

In the present embodiment, in a case where a tomographic image group is displayed on the display unit 78, a tomographic image of a predetermined tomographic plane (for example, a first tomographic plane from the top) in the tomographic image group is displayed as an initial image. Further, the display is switched to a tomographic image on a different tomographic plane by a user operation (for example, a scroll operation, a click operation, and the like, using a mouse). As shown in FIG. 16, in the present embodiment, a scroll bar SB is displayed in a tomographic image display area so as to identify which tomographic plane a tomographic image to be displayed is on.

Figure 17:
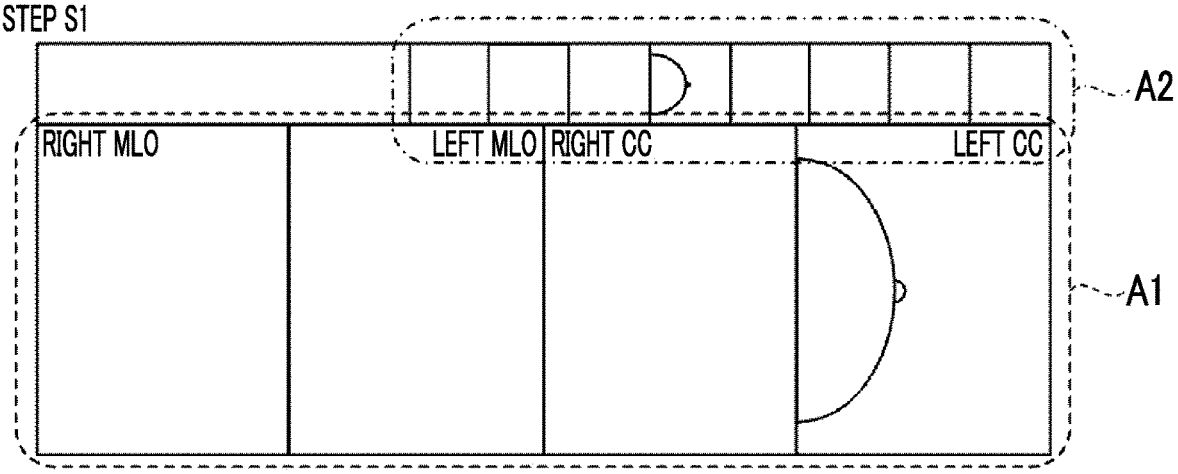
FIG. 17 is a diagram showing an example of a display screen.
Figure 17:
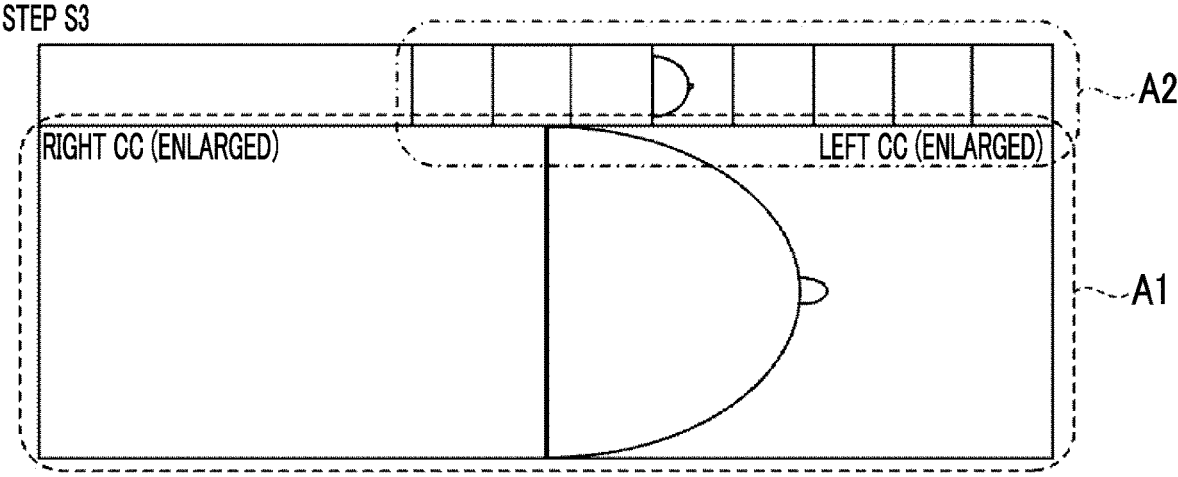

In each of the display steps, in a case where at least one of images to be displayed has not been received, the display control unit 94 performs a control for skipping the display of the unreceived image and displaying only the received image. Accordingly, for example, at a time point when the reception unit 90 receives the composite 2-dimensional image of the left CC, only the composite 2-dimensional image of the left CC is displayed in the display step S1 as shown in FIG. 17. Further, at this time point, in a case where the user performs an operation of displaying the next display step after the display step S1, since all the images to be displayed in the display step S2 have not been received, the display step S2 is not executed, and the display step S3 is executed. Thus, as shown in FIG. 17, an enlarged image in which the breast portion of the composite 2-dimensional image of the left CC is enlarged is displayed. Whenever the reception of the composite 2-dimensional image by the reception unit 90 is completed, and whenever the generation of the tomographic image group by the generating unit 92 is completed, the number of images capable of being displayed in each step increases.

Figure 18:
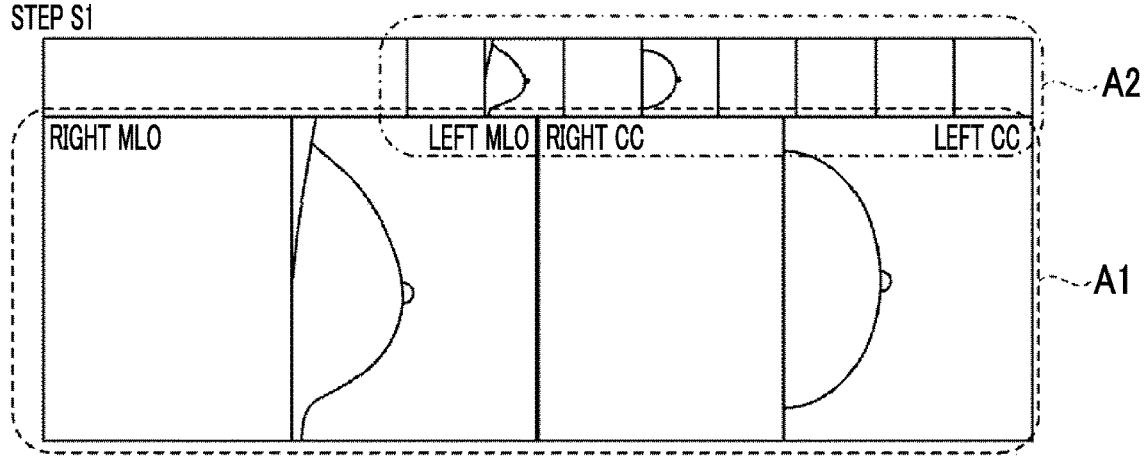
FIG. 18 is a diagram showing an example of a display screen.

For example, in a case where the image interpretation support apparatus 16 receives a composite 2-dimensional image of the left MLO before generating a tomographic image group of the left CC, a screen shown in FIG. 18 is displayed on the display unit 78 in the display step S1. As shown in FIG. 18, in this case, in the display step S1, the composite 2-dimensional image of the left MLO and the composite 2-dimensional image of the left CC are displayed on the display unit 78.

Figure 19:
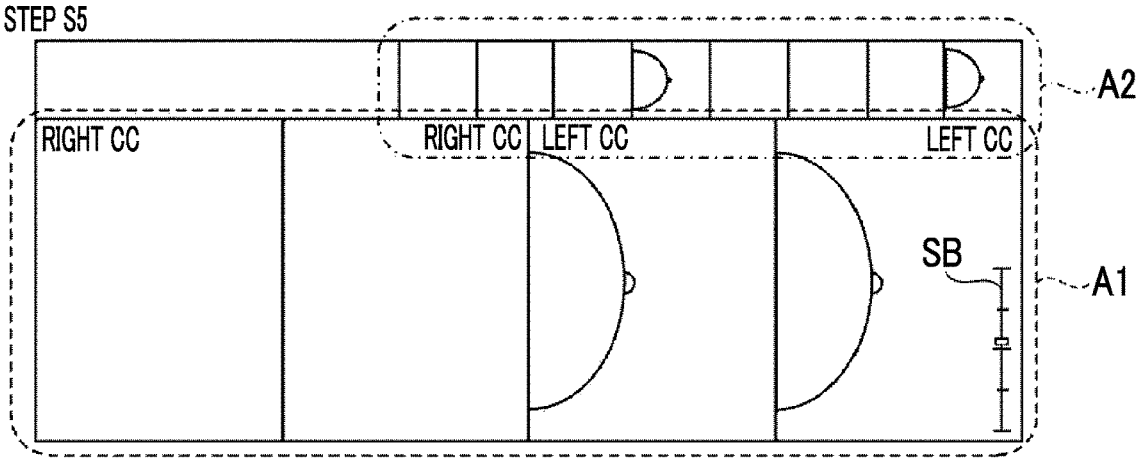
FIG. 19 is a diagram showing an example of a display screen.

On the other hand, in a case where the image interpretation support apparatus 16 generates the tomographic image group of the left CC before receiving the composite 2-dimensional image of the left MLO, a screen shown in FIG. 19 is displayed on the display unit 78 in the display step S5. As shown in FIG. 19, in this case, in the display step S5, the composite 2-dimensional image of the left CC and the tomographic image group of the left CC are displayed on the display unit 78. In a case where the user performs an operation of displaying a screen of the next display step on the screen displayed on the display unit 78, the next display step including a displayable image is executed.

Further, the display control unit 94 performs a control for further displaying a list of all image types displayed according to the display rule on the display unit 78. As shown in FIGS. 17 to 19, the display screen according to the present embodiment includes a display area A1 in which an image according to the display rule is displayed, and a display area A2 of a list of all image types displayed according to the display rule. The display area A2 includes display areas of thumbnails of total eight types of images including composite 2-dimensional images of the right MLO, the left MLO, the right CC, and the left CC and tomographic image groups of the right MLO, the left MLO, the right CC, and the left CC.

The display control unit 94 performs a control for identifiably displaying images that can be displayed according to the display rule and images that cannot be displayed according to the display rule, in the list of the display area A2. Specifically, for example, the display control unit 94 performs a control for displaying thumbnails of images that can be displayed according to the display rule and hiding images that cannot be displayed according to the display rule, in the list of the display area A2. Here, the images that can be displayed (displayable images) mean composite 2-dimensional images that have been received by the reception unit 90 and a tomographic image group that has been generated by the generating unit 92.

Figure 20:
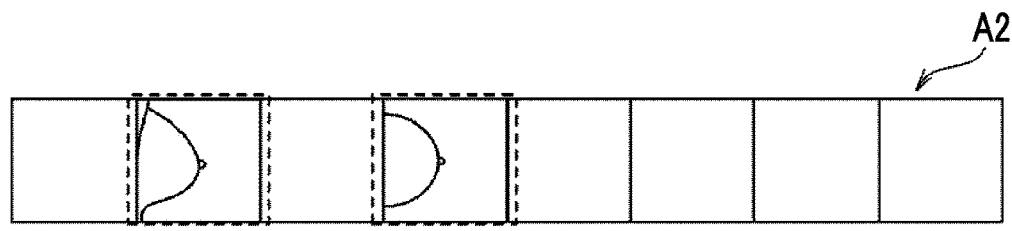
FIG. 20 is a diagram showing an example of a display mode of a display area of a list of image types.

As shown in FIG. 20, the display control unit 94 may emphasize the displayable images by performing a control for blinking frame lines of the displayable images (dashed-line rectangles in the example of FIG. 20), for example.

Figure 21:
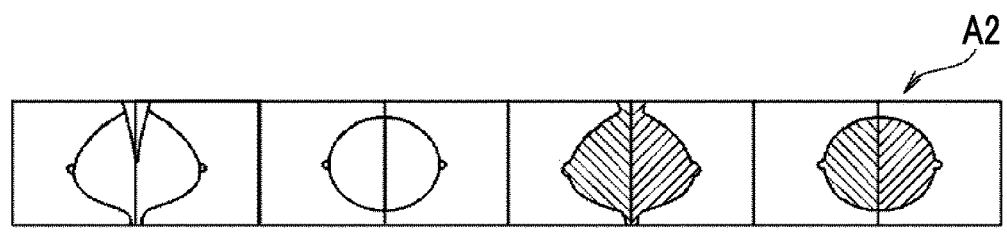
FIG. 21 is a diagram showing an example of a display mode of a display area of a list of image types.

In addition, as shown in FIG. 21, the display control unit 94 may perform a control for identifiably displaying images that can be displayed according to the display rule and images that cannot be displayed according to the display rule by performing a control for displaying thumbnails for the displayable images and displaying schema diagrams (indicated by hatching in the example of FIG. 21) for the non-displayable images.

The acceptance unit 96 accepts an operation of ending display on the display unit 78 from the user. For example, in a case where the user determines that the image interpretation has been completed and wants to end the display, the user presses an end button (not shown) as the operation of ending the display.

Figure 22:
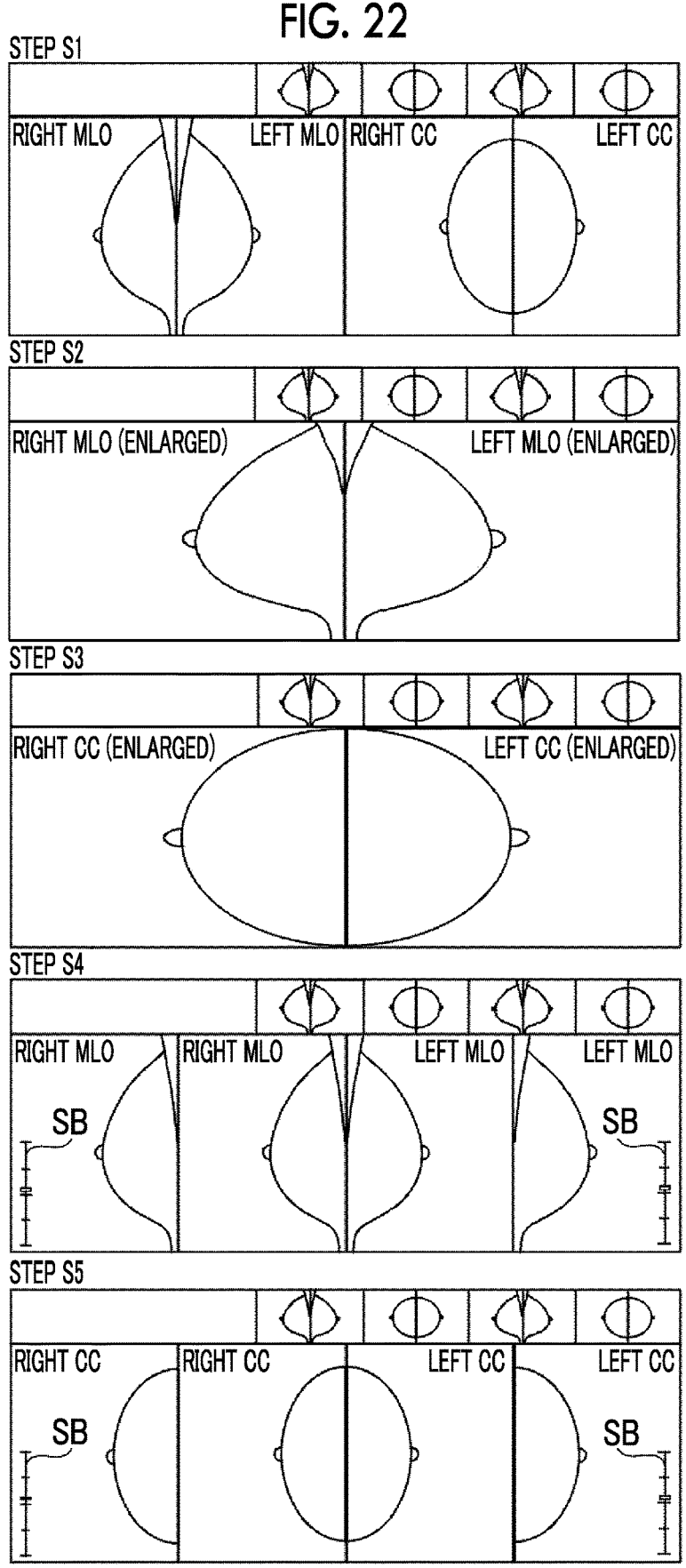
FIG. 22 is a diagram showing an example of a state in which all images to be displayed in respective display steps are displayed.

The determination unit 98 determines whether all the images to be displayed in the respective display steps have been displayed on the display unit 78. For example, the determination unit 98 specifies all the images to be displayed from an imaging order acquired from the RIS or the like, and determines whether all the specified images have been displayed on the display unit 78 under the control of the display control unit 94. The determination unit 98 may determine whether all the images to be displayed in the respective display steps have been displayed on the display unit 78 by determining whether or not an image that can be finally displayed (in the flow of FIGS. 8 and 13, for example, a tomographic image group of the right MLO) is displayed on the display unit 78 under the control of the display control unit 94. FIG. 22 shows an example of a state in which all images to be displayed in respective display steps are displayed on the display unit 78.

Figure 23:
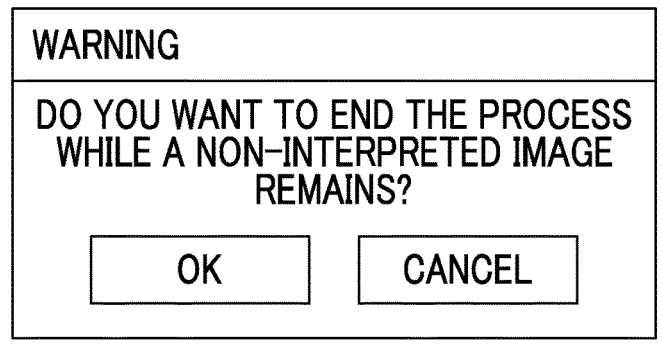
FIG. 23 is a diagram showing an example of a warning screen.

The notification unit 99 notifies user of a warning in a case where the acceptance unit 96 accepts the operation of ending the display before the determination unit 98 determines that all the images to be displayed in the respective display steps have been displayed on the display unit 78. Specifically, in this case, the notification unit 99 notifies the user of a warning by displaying a message indicating that there is an image that has not been displayed on the display unit 78, as shown in FIG. 23, as an example. Further, on this warning notification screen, buttons for confirming whether or not to end the display ("OK" button and "cancel" button in the example of FIG. 23) are displayed. The notification unit 99 may notify the user of a warning by voice. In a case where the determination unit 98 determines that all the images to be displayed in the respective display steps have been displayed on the display unit 78, the notification unit 99 may notify that the display of all the images has been completed.

Figure 24:
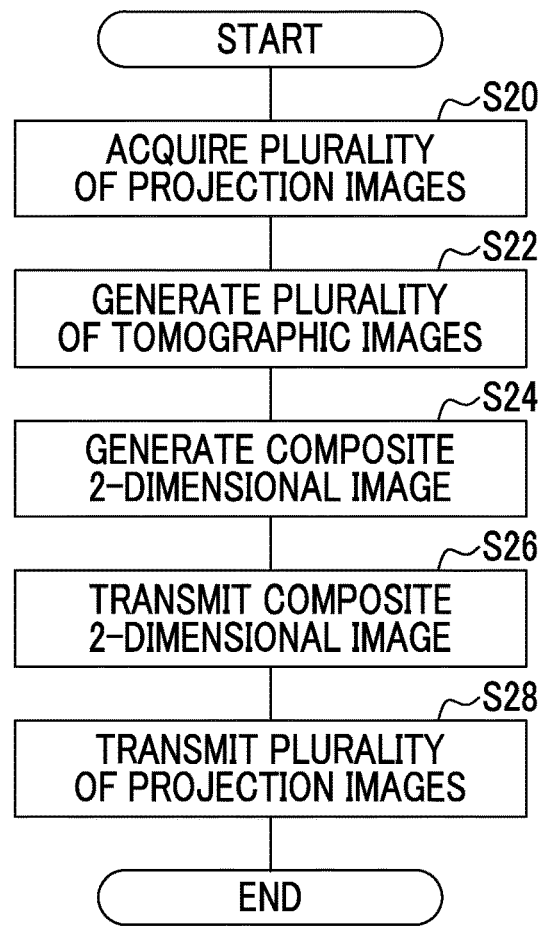
FIG. 24 is a flowchart showing an example of an image transmitting process.

Next, operations of the console 14 and the image interpretation support apparatus 16 according to the present embodiment will be described with reference to FIGS. 24 to 26. As the CPU 50A of the console 14 executes the control processing program 51, an image transmitting process shown in FIG. 24 is executed. As the CPU 70A of the image interpretation support apparatus 16 executes the image processing program 71, an image receiving process shown in FIG. 25 and a display control process shown in FIG. 26 are executed. The image transmitting process shown in FIG. 24 is executed for each of the plurality of projection images obtained in the respective steps of the tomosynthesis imaging process shown in FIG. 8. The image receiving process shown in FIG. 25 and the display control process shown in FIG. 26 are executed in parallel in at least a part thereof.

In step S20 of FIG. 24, the projection image acquisition unit 80 acquires, through the control unit 20 of the mammography apparatus 12, a plurality of projection images respectively corresponding to the plurality of irradiation positions t and obtained by tomosynthesis imaging. In step S22, as described above, the composite 2-dimensional image generating unit 82 generates a plurality of tomographic images at a predetermined slice interval by performing reconstruction using the plurality of projection images acquired in the processing of step S20.

In step S24, the composite 2-dimensional image generating unit 82 generates a composite 2-dimensional image on the basis of the plurality of tomographic images generated by the processing in step S22, as described above. In step S26, the transmission unit 84 transmits the composite 2-dimensional image generated by the processing in step S24 to the image interpretation support apparatus 16. In step S28, the transmission unit 84 transmits the plurality of projection images acquired by the processing in step S20 to the image interpretation support apparatus 16. In a case where the process of step S28 ends, the image transmitting process ends. The transmission of the composite 2-dimensional image in step S26 and the transmission of the plurality of projection images in step S28 may be executed as the user confirms the images and then gives a transmission instruction. The transmission of the composite 2-dimensional image in step S26 and the transmission of the plurality of projection images in step S28 may be executed after all images are generated for the four sets of the right MLO, the left MLO, the right CC, and the left CC.

Figure 25:
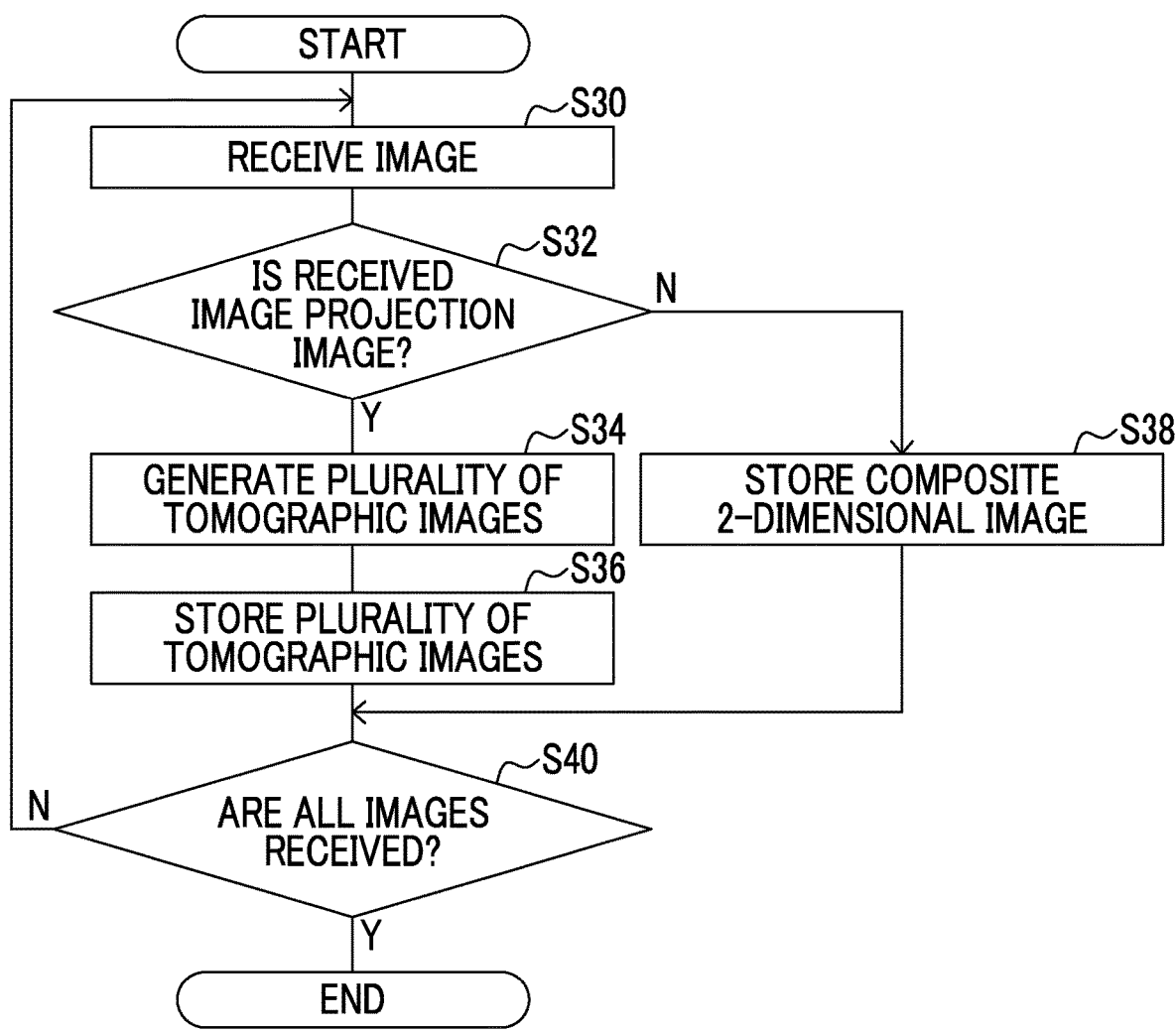
FIG. 25 is a flowchart showing an example of an image receiving process.
Figure 26:
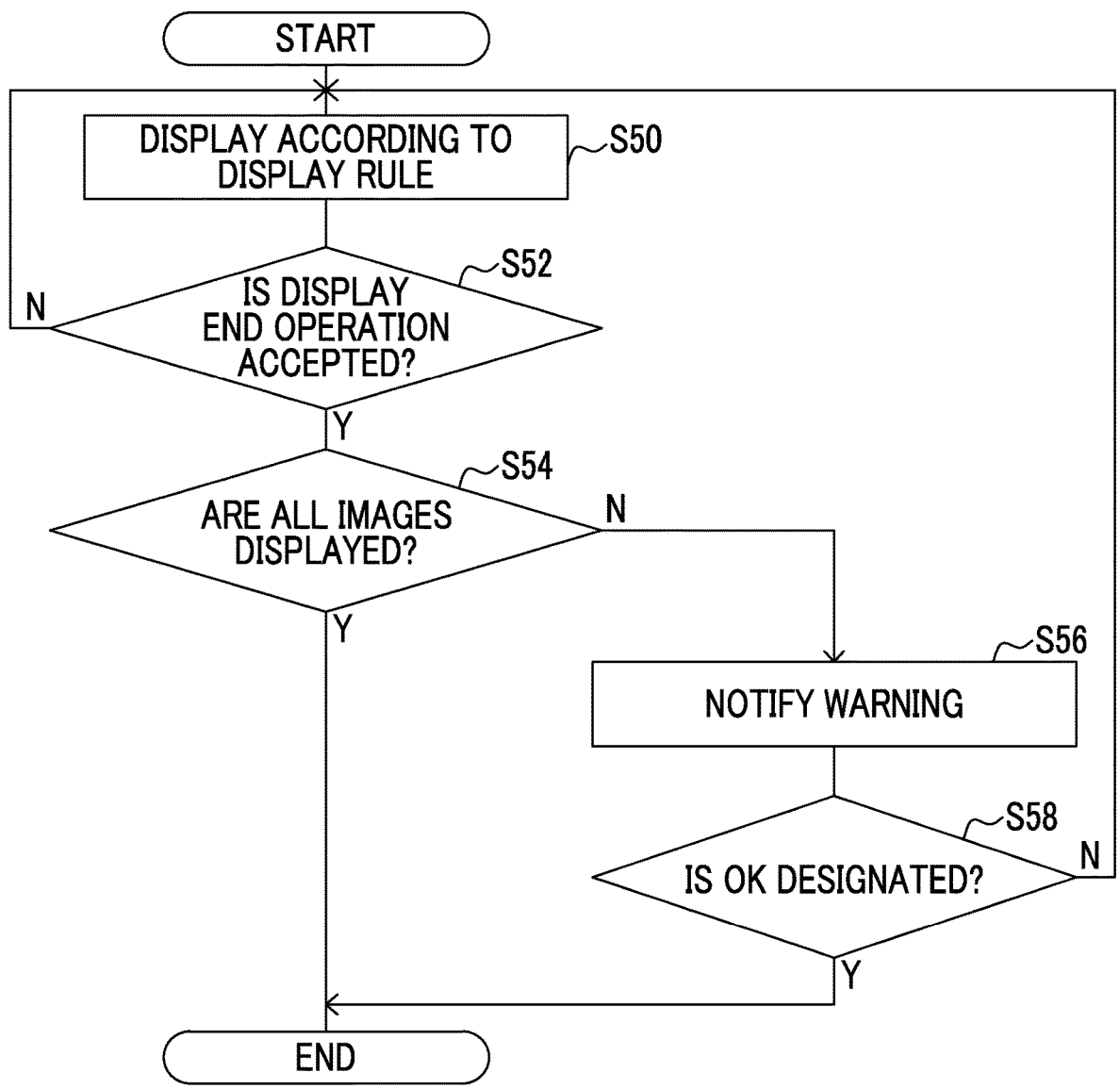
FIG. 26 is a flowchart showing an example of a display control process.

In step S30 of FIG. 25, the reception unit 90 receives the images transmitted by the console 14. The images received in step S30 are the composite 2-dimensional images transmitted in step S26 or the plurality of projection images transmitted in step S28. In step S32, the reception unit 90 determines whether the images received in step S30 are the plurality of projection images. In a case where this determination is affirmative, the procedure proceeds to step S34.

In step S34, as described above, the generating unit 92 generates a plurality of tomographic images on the basis of the plurality of projection images received by the process of step S30. In step S36, the generating unit 92 stores the plurality of tomographic images generated by the process of step S34 in the storage unit 72. In a case where the process of step S36 ends, the procedure proceeds to step S40.

On the other hand, in a case where the images received in step S30 are composite 2-dimensional images, the determination in step S32 is negative, and the procedure proceeds to step S38. In step S38, the reception unit 90 stores the composite 2-dimensional images received by the process of step S30 in the storage unit 72. In a case where the process of step S38 ends, the procedure proceeds to step S40. The plurality of tomographic images stored in the storage unit 72 in step S36 and the composite 2-dimensional images stored in the storage unit 72 in step S38 are used in step S50 of FIG. 26 to be described below.

In step S40, the reception unit 90 determines whether all the images have been received in step S30. Here, all the images mean four sets of projection image groups of the left CC, the left MLO, the right CC, and the right MLO, and four composite 2-dimensional images of the left CC, the left MLO, the right CC, and the right MLO. In a case where this determination is negative, the procedure returns to step S30, and in a case where the determination is affirmative, the image receiving process ends.

In step S50 of FIG. 26, the display control unit 94 performs a control for displaying the plurality of tomographic images and the composite 2-dimensional images stored in the storage unit 72 on the display unit 78 in accordance with a preset display rule, as described above. Here, in each of the display steps 1 to 5, for example, as shown in FIGS. 17 to 19, the display control unit 94 performs, in a case where at least one of images to be displayed has not been received (that is, is not stored in the storage unit 72), a control for skipping display of the unreceived image and displaying only received images. Further, as described above, the display control unit 94 performs a control for displaying a list of all image types displayed according to the display rule on the display unit 78.

In step S52, the acceptance unit 96 determines whether or not an operation of ending display on the display unit 78 from the user has been accepted. In a case where this determination is negative, the procedure returns to step S50, and in a case where this determination is affirmative, the procedure proceeds to step S54. For example, in a case where the user performs an operation of displaying a screen of the next display step, the determination in step S52 is negative. In this case, in step S50, the screen of the next display step is displayed on the display unit 78 according to the display rule. In step S54, the determination unit 98 determines whether all the images to be displayed in the respective display steps have been displayed on the display unit 78, as described above. In a case where this determination is negative, the procedure proceeds to step S56.

In step S56, the notification unit 99 notifies the user of a warning as described above. In step S58, the acceptance unit 96 determines whether or not the user has designated the "OK" button on a warning display screen shown in FIG. 23. In a case where the "cancel" button is designated by the user, the determination in step S58 is negative, and the procedure returns to step S50. On the other hand, in a case where the determination in step S58 is affirmative, the display control process ends. In a case where the determination in step S54 is affirmative, similarly, the display control process ends.

As described above, according to the present embodiment, the console 14 does not transmit a relatively large number of tomographic images to the image interpretation support apparatus 16, but transmits a plurality of projection images and composite 2-dimensional images to the image interpretation support apparatus 16. Accordingly, the communication load is reduced, and as a result, it is possible to reduce a user's standby time compared with a case where tomographic images are transmitted. This is because the number of tomographic images is generally larger than the number of projection images.

Further, according to the present embodiment, the console 14 transmits a plurality of projection images to the image interpretation support apparatus 16 after transmitting composite 2-dimensional images to the image interpretation support apparatus 16. Accordingly, the user of the image interpretation support apparatus 16 can interpret the composite 2-dimensional images without waiting for generation of a plurality of tomographic images by reconstruction using the plurality of projection images. In addition, it is possible to generate a plurality of tomographic images by reconstruction using a plurality of projection images while composite 2-dimensional images are being interpreted, and to interpret the plurality of tomographic images immediately after the completion of the interpretation of the composite 2-dimensional images. As a result, it is possible to further reduce the user's standby time.

Figure 27:
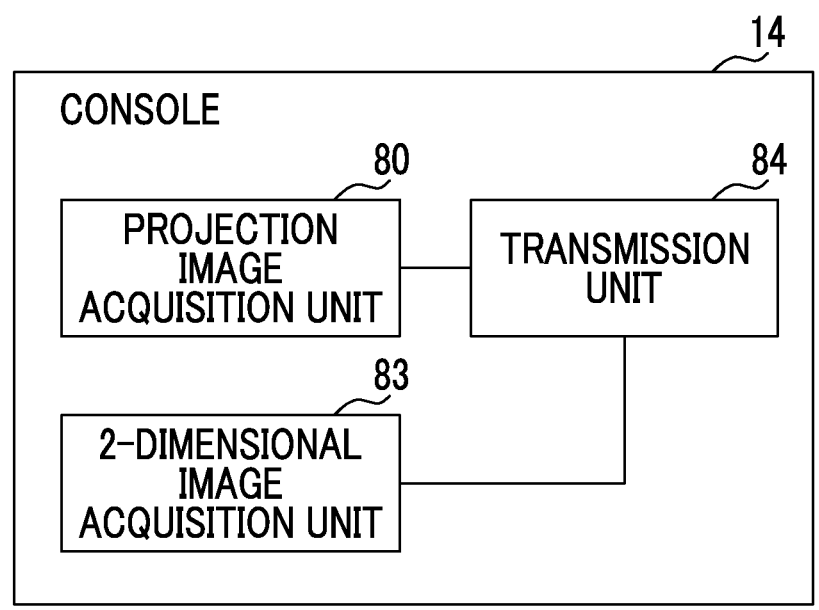
FIG. 27 is a block diagram showing an example of a functional configuration of a console according to a modification example.

In the above embodiment, instead of a composite 2-dimensional image, a 2-dimensional image obtained by irradiating a subject with radiation having a higher dose than in tomosynthesis imaging at one position (for example, a position on a normal passing through the center of the detection surface of the radiation detector 30) from the radiation source 36R, so-called simple imaging, may be used. In this case, as shown in FIG. 27, the console 14 includes a 2-dimensional image acquisition unit 83 that acquires a 2-dimensional image obtained by the mammography apparatus 12 by simple imaging, instead of the composite 2-dimensional image generating unit 82 in the above embodiment. In this case, the transmission unit 84 transmits the 2-dimensional images acquired by the 2-dimensional image acquisition unit 83 to the image interpretation support apparatus 16, and transmits the plurality of projection images acquired by the projection image acquisition unit 80 to the image interpretation support apparatus 16. Further, in the above embodiment, both a composite 2-dimensional image and a 2-dimensional image obtained by the simple imaging may be used instead of a composite 2-dimensional image.

In the above embodiment, in a case where at least one of images to be displayed in respective display steps can be displayed, the display control unit 94 executes a corresponding display step even in a case where all the images cannot be displayed, but the present invention is not limited to thereto. For example, the display control unit 94 may execute the display steps only in a case where all the images to be displayed in the respective display steps can be displayed.

In the above-described embodiment, for example, as a hardware structure of processing units that execute various types of processes, such as each functional unit of the console 14 and each functional unit of the image interpretation support apparatus 16, various processors to be described hereinafter may be used. As described above, the various processors may include the CPU which is a general-purpose processor that executes software (programs) and functions as a variety of processing units, a programmable logic device (PLD) of which a circuit configuration is changeable after manufacturing, such as an FPGA, a dedicated electric circuit that is a processor having a circuit configuration that is dedicatedly designed for executing a specific process, such as an application specific integrated circuit (ASIC), or the like.

One processing unit may be configured by one processor among the variety of processors described above, or may be configured by a combination of the same type or different types of two or more processors (for example, a combination of plural FPGAs or a combination of a CPU and an FPGA). Further, a plurality of processing units may be configured by one processor.

As an example in which the plurality of processing units are configured by one processor, first, as represented by a computer such as a client or a server, a configuration in which a combination of one or more CPUs and software forms one processor and this processor functions as a plurality of processing units may be employed. Second, as represented by a system-on-chip (SoC) or the like, a configuration in which a processor for realizing entire functions of a system including a plurality of processing units using one integrated circuit (IC) chip is used may be employed. As described above, the various processing units are configured using one or more of the above-described various processors as a hardware structure.

Further, as the hardware structure of the variety of processors is, more specifically, electric circuitry in which circuit elements such as semiconductor elements are combined may be employed.

Further, in the above embodiment, a configuration in which the control processing program 51 is stored (installed) in the ROM 50B in advance has been described, but the present invention is not limited to thereto. The control processing program 51 may be provided in the form of being recorded on a recording medium such as a CD-ROM (Compact Disc Read Only Memory), a DVD-ROM (Digital Versatile Disc Read Only Memory), or a USB (Universal Serial Bus) memory. Further, the control processing program 51 may be downloaded from an external device through a network.

Further, in the above-described embodiment, a configuration in which the image processing program 71 is stored (installed) in the ROM 70B in advance has been described, but the present invention is not limited thereto. The image processing program 71 may be provided in the form of being recorded on a recording medium such as a CD-ROM, a DVD-ROM, and a USB memory. The image processing program 71 may be downloaded from an external device through a network.

EXPLANATION OF REFERENCES

10: Radiation imaging system
12: mammography apparatus
14: console
16: image interpretation support apparatus
20, 50, 70: control unit
20A, 50A, 70A: CPU
20B, 50B, 70B: ROM
20C, 50C, 70C: RAM
21: imaging processing program
22, 52, 72: storage unit
24, 54, 74: I/F unit
26, 56, 76: operation unit
30: radiation detector
31: motor
32: compression plate driving unit
33: compression force detection sensor
34: compression plate
36: radiation irradiation unit
36R: radiation source
37: radiation source driving unit
38: ball screw
39, 59, 79: bus
40: imaging table
40A: imaging plane
42: arm unit
44: base
45: shaft
46: compression unit
51: control processing program
58, 78: display unit
71: image processing program
80: projection image acquisition unit
82: composite 2-dimensional image generating unit
83: 2-dimensional image acquisition unit
84: transmission unit
90: reception unit
92: generating unit
94: display control unit
96: acceptance unit
98: determination unit
99: notification unit
A1, A2: display area
R: radiation
SB: scroll bar
t: irradiation position
θ: angle

What is claimed is:

1. A radiation imaging system comprising:
a transmission device; and
a reception device,
wherein the transmission device includes a first non-transitory storage device and a first processor, and the first processor by executing a first program stored in the first non-transitory device to:
acquire a plurality of projection images respectively corresponding to a plurality of positions and obtained by tomosynthesis imaging in which a subject is irradiated with radiation from a radiation source at the plurality of positions;
generate a plurality of tomographic images by reconstruction using the plurality of projection images and generate a composite 2-dimensional image on the basis of the plurality of tomographic images, or acquire a 2-dimensional image obtained by irradiating the subject with radiation having a higher dose than that in the tomosynthesis imaging from the radiation source at one position; and
transmit at least one of the composite 2-dimensional image or the 2-dimensional image to the reception device, and transmit the plurality of projection images to the reception device; and wherein the reception device includes a second non-transitory storage device and a second processor, and the second processor by executing a second program stored in the second non-transitory storage device to:

receive at least one of the composite 2-dimensional image or the 2-dimensional image transmitted by the transmission device, and the plurality of projection images;

generate the plurality of tomographic images by reconstruction using the plurality of projection images; and perform a control for displaying at least one of the composite 2-dimensional image or the 2-dimensional image, and the tomographic image on a display unit.

2. The radiation imaging system according to claim 1, wherein the first processor further executes the first program to transmit at least one of the composite 2-dimensional image or the 2-dimensional image to the reception device, and then, transmits the plurality of projection images to the reception device.

3. The radiation imaging system according to claim 2, wherein the second processor further executes the second program to perform the control for displaying at least one of the composite 2-dimensional image or the 2-dimensional image, and the tomographic image on the display unit according to a preset display rule.

4. The radiation imaging system according to claim 3, wherein thee the second processor further executes the second program to perform a control for further displaying a list of all image types displayed according to the display rule on the display unit.

5. The radiation imaging system according to claim 1, wherein the first processor further executes the first program to transmit the plurality of projection images to the reception device, and then, transmits at least one of the composite 2-dimensional image or the 2-dimensional image to the reception device.

6. The radiation imaging system according to claim 5, wherein the second processor further executes the second program to perform the control for displaying at least one of the composite 2-dimensional image or the 2-dimensional image, and the tomographic image on the display unit according to a preset display rule.

7. The radiation imaging system according to claim 1, wherein the second processor further executes the second program to perform the control for displaying at least one of the composite 2-dimensional image or the 2-dimensional image, and the tomographic image on the display unit according to a preset display rule.

8. The radiation imaging system according to claim 7, wherein the display rule includes an execution order of a plurality of display steps, and the number and type of images to be displayed in each display step.

9. The radiation imaging system according to claim 8, wherein the plurality of display steps include a display step of displaying at least one of the composite 2-dimensional image or the 2-dimensional image at a preset display position, and the display step of displaying both of at least one of the composite 2-dimensional image or the 2-dimensional image and the tomographic image at the display position.

10. The radiation imaging system according to claim 9, wherein the second processor further executes the second program to perform, in each of the display steps, in a case where at least one of images to be displayed has not been received, the control for skipping display of the unreceived image and displaying only the received image.

11. The radiation imaging system according to claim 9, wherein the second processor of the reception device further executes the second program to:

accept an operation of ending display on the display unit from a user;

determine whether all images to be displayed in the respective display steps have been displayed on the display unit; and notify the user of a warning, in a case where the second processor accepts the operation of ending the display before the second processor determines that all the images to be displayed in the respective display steps have been displayed on the display unit.

12. The radiation imaging system according to claim 9, wherein the second processor of the reception device further executes the second program to:

determine whether all images to be displayed in the respective display steps have been displayed on the display unit; and notify that the display is completed, in a case where the second processor determines that all the images to be displayed in the respective display steps have been displayed on the display unit.

13. The radiation imaging system according to claim 8, wherein the second processor further executes the second program to perform, in each of the display steps, in a case where at least one of images to be displayed has not been received, the control for skipping display of the unreceived image and displaying only the received image.

14. The radiation imaging system according to claim 13, wherein the second processor of the reception device further executes the second program to:

accept an operation of ending display on the display unit from a user;

determine whether all images to be displayed in the respective display steps have been displayed on the display unit; and notify the user of a warning, in a case where the second processor accepts the operation of ending the display before the second processor determines that all the images to be displayed in the respective display steps have been displayed on the display unit.

15. The radiation imaging system according to claim 13, wherein the second processor of the reception device further executes the second program to:

determine whether all images to be displayed in the respective display steps have been displayed on the display unit; and notify that the display is completed, in a case where the second processor determines that all the images to be displayed in the respective display steps have been displayed on the display unit.

16. The radiation imaging system according to claim 8, wherein the second processor of the reception device further executes the second program to:

accept an operation of ending display on the display unit from a user;

determine whether all images to be displayed in the respective display steps have been displayed on the display unit; and notify the user of a warning, in a case where the second processor accepts the operation of ending the display before the second processor determines that all the images to be displayed in the respective display steps have been displayed on the display unit.

17. The radiation imaging system according to claim 8,
wherein the second processor of the reception device further executes the second program to:
determine whether all images to be displayed in the respective display steps have been displayed on the display unit; and
notify that the display is completed, in a case where the second processor determines that all the images to be displayed in the respective display steps have been displayed on the display unit.

18. The radiation imaging system according to claim 7,
wherein the the second processor further executes the second program to perform a control for further displaying a list of all image types displayed according to the display rule on the display unit.

19. The radiation imaging system according to claim 18,
wherein images that can be displayed according to the display rule and images that cannot be displayed according to the display rule are identifiably displayed in the list.

20. A transmission device comprising a non-transitory storage device and a processor, wherein the processor executes a program stored in the non-transitory storage device to:
acquire a plurality of projection images respectively corresponding to a plurality of positions and obtained by tomosynthesis imaging in which a subject is irradiated with radiation from a radiation source at the plurality of positions;
generate a plurality of tomographic images by reconstruction using the plurality of projection images and generate a composite 2-dimensional image on the basis of the plurality of tomographic images, or acquire a 2-dimensional image obtained by irradiating the subject with radiation having a higher dose than that in the tomosynthesis imaging from the radiation source at one position; and
transmit at least one of the composite 2-dimensional image or the 2-dimensional image to the reception device, and transmit the plurality of projection images to the reception device.

* * * * *